United States Patent
Barenholz et al.

(10) Patent No.: US 11,123,293 B2
(45) Date of Patent: Sep. 21, 2021

(54) LIPOSOMAL FORMULATION FOR JOINT LUBRICATION

(71) Applicant: MOEBIUS MEDICAL LTD., Tel Aviv (IL)

(72) Inventors: Yechezkel Barenholz, Jerusalem (IL); Yaniv Dolev, Raanana (IL); Keren Turjeman, Jerusalem (IL); Gadi Sarfati, Beit Guvrin (IL); Maty Ayal-Hershkovitz, Herzliya (IL)

(73) Assignee: Moebius Medical Ltd., Tel Aviv (IL)

( * ) Notice: Subject to any disclaimer, the term of this patent is extended or adjusted under 35 U.S.C. 154(b) by 0 days.

(21) Appl. No.: 16/337,188

(22) PCT Filed: Aug. 21, 2018

(86) PCT No.: PCT/IL2018/050923
§ 371 (c)(1),
(2) Date: Mar. 27, 2019

(87) PCT Pub. No.: WO2019/038763
PCT Pub. Date: Feb. 28, 2019

(65) Prior Publication Data
US 2020/0170948 A1 Jun. 4, 2020

Related U.S. Application Data

(60) Provisional application No. 62/548,429, filed on Aug. 22, 2017.

(51) Int. Cl.
*A61K 9/127* (2006.01)
*A61K 31/685* (2006.01)
(Continued)

(52) U.S. Cl.
CPC ............ *A61K 9/127* (2013.01); *A61K 31/685* (2013.01); *A61K 47/10* (2013.01); *A61K 47/26* (2013.01)

(58) Field of Classification Search
CPC ...... A61K 9/127; A61K 47/26; A61K 31/685; A61K 47/10; A61K 9/0019; A61K 31/047;
(Continued)

(56) References Cited

U.S. PATENT DOCUMENTS 5,403,592 A    4/1995  Hills
5,941,909 A *  8/1999  Purkait ............... A61F 2/12
                                                623/23.72
(Continued)

FOREIGN PATENT DOCUMENTS

CN    101027065 A    8/2007
CN    104688721 A    6/2015
(Continued)

OTHER PUBLICATIONS

Sarma, A.V., et al in Journal of Orthopaedic Research, 19, pp. 671-676, 2001.*
(Continued)

*Primary Examiner* — Gollamudi S Kishore
(74) *Attorney, Agent, or Firm* — Allan A. Fanucci

(57) ABSTRACT

The present invention provides a pharmaceutical composition for the lubrication of joints, the pharmaceutical composition comprising a non-ionic tonicity agent comprising a polyol, and liposomes comprising at least one membrane comprising at least one phospholipid (PL) selected from a glycerophospholipid (GPL), said GPL having two C12-C18 hydrocarbon chains, being the same or different, and sphingomyelin (SM) having a C12-C18 hydrocarbon chain, the pharmaceutical composition being essentially free of an additional pharmaceutically active agent, wherein the at least one membrane has a phase transition temperature in the range of about 20° C. to about 39° C. and the joint has a joint temperature which is above the phase transition temperature.

20 Claims, 7 Drawing Sheets

(51) Int. Cl.
    *A61K 47/10* (2017.01)
    *A61K 47/26* (2006.01)
(58) Field of Classification Search
    CPC .. A61L 27/54; A61L 2300/22; A61L 2430/06;
        A61L 2400/06; A61L 2400/10; A61L
        2430/24; A61L 27/50; A61P 19/02
    See application file for complete search history.

(56) References Cited

U.S. PATENT DOCUMENTS

| | | | |
|---|---|---|---|
| 6,133,249 A | 10/2000 | Hills | |
| 6,379,648 B1 * | 4/2002 | Day | C03C 3/15 424/1.29 |
| 6,800,298 B1 | 10/2004 | Burdick | |
| 7,749,485 B2 | 7/2010 | Tournier | |
| 8,071,137 B2 | 12/2011 | Dhanaraj | |
| 8,623,839 B2 | 1/2014 | Su | |
| 8,895,054 B2 * | 11/2014 | Barenholz | A61K 9/0019 424/450 |
| 8,951,991 B2 | 2/2015 | Paoletti | |
| 2002/0142048 A1 | 10/2002 | Sands | |
| 2004/0047807 A1 * | 3/2004 | Meyer | A61K 31/05 424/9.42 |
| 2005/0069576 A1 | 3/2005 | Mills | |
| 2005/0123593 A1 | 6/2005 | Thompson | |
| 2005/0164981 A1 | 7/2005 | Burdick | |
| 2006/0029655 A1 | 2/2006 | Barenholz | |
| 2008/0027554 A1 * | 1/2008 | Talmadge | A61L 27/227 623/17.16 |
| 2009/0232883 A1 * | 9/2009 | Yoshino | A61K 9/1271 424/450 |
| 2011/0171288 A1 | 7/2011 | Mohammadi | |
| 2012/0213844 A1 | 8/2012 | Huang | |
| 2013/0142863 A1 | 6/2013 | Klein | |
| 2014/0038917 A1 | 2/2014 | Gavard Molliard | |

FOREIGN PATENT DOCUMENTS

| | | |
|---|---|---|
| CN | 105377238 A | 3/2016 |
| WO | 02078445 A1 | 10/2002 |
| WO | 03000190 A2 | 1/2003 |
| WO | 03000191 A2 | 1/2003 |
| WO | 2004047792 A2 | 6/2004 |
| WO | 2008038292 A2 | 4/2008 |
| WO | 2009024670 A2 | 2/2009 |
| WO | 2011158237 A1 | 12/2011 |
| WO | 2012001679 A1 | 1/2012 |
| WO | 2012143876 A1 | 10/2012 |
| WO | 2013/153221 * | 10/2013 |

OTHER PUBLICATIONS

Akerman and Kopp (1987) Intra-articular and skin surface temperature of human temporomandibular joint. Scand J Dent Res 95(6): 493-498.
Ballantine and Stachowiak (2002) The effects of lipid depletion on osteoarthritic wear. Wear 253(3-4): 385-393.
Chernos (2016) A rheological study of treatments for osteoarthritis. A thesis submitted to the faculty of graduate and postdoctoral studies (Biomedical Engineering); University of British Columbia, Vancouver, Canada. 112 pages.
Conrozier et al., (2014) Role of high concentrations of mannitol on the stability of hyaluronan in an oxidative stress model induced by xanthine/xanthine oxidase. Osteoarthritis and Cartilage 22: S478.
Conrozier et al., (2016) Safety and efficacy of intra-articular injections of a combination of hyaluronic acid and mannitol (HAnOX-M) in patients with symptomatic knee osteoarthritis: Results of a double-blind, controlled, multicenter, randomized trial. The Knee 23(5): 842-848.
Eymard et al., (2016) Addition of Mannitol to Hyaluronic Acid may Shorten Viscosupplementation Onset of Action in Patients with Knee Osteoarthritis: Post-Hoc Analysis of a Double-blind, Controlled Trial. J Clin Exp Orthop 2: 21; 6 pages.
Feraccioli et al., (1981) Decrease of osteoarthritic synovial fluid viscosity by means of U.V. illumination: a method to evaluate the free radical scavenging action of drugs. Biochem Pharmacol 30(13): 1805-1808.
Forsey et al., (2006) The effect of hyaluronic acid and phospholipid based lubricants on friction within a human cartilage damage model. Biomaterials 27(26): 4581-4590.
Hills and Butler (1984) Surfactants identified in synovial fluid and their ability to act as boundary lubricants. Annals of the Rheumatic Diseases 43: 641-648.
Hills and Monds (1998) Deficiency of lubricating surfactant lining the articular surfaces of replaced hips and knees. British Journal of Rheumatology 37: 143-147.
Hills and Crawford (2003) Normal and prosthetic synovial joints are lubricated by surface-active phospholipid: a hypothesis. J Arthroplasty 18(4): 499-505.
Hills et al., (1998) Release of lubricating synovial surfactant by intra-articular steroid. Br J Rheumatol 37(6): 649-652.
Hollander and Moore (1956) Studies in Osteo-Arthritis using Intra-Articular Temperature Response to Injection of Hydrocortisone Acetate and Prednisone. Ann Rheum Dis 15(4): 320-326.
Jones et al., (2004) The Effect of Surface Active Phospholipids on the Lubrication of Osteoarthritic Sheep Knee Joints: Wear. Tribology Letters 16(4): 291-296.
Kandel et al., (2014) Safety and Efficacy of Liposome Intra-Articular Injection in Moderate Knee Osteoarthritis. a Prospective Randomized Double-Blinded Study; Abstract No. 2234. 2014 ACR/ARHP Annual Meeting, Nov. 14-19, 2014 in Boston, MA, USA. 3 pages.
Kandel et al., (2014) Safety and efficacy of MM-II, an intra-articular injection of liposomes, in moderate knee osteoarthritis. Prospective randomized double-blinded study. Osteoarthritis and Cartilage 22 (Supplement): S193.
Kandel et al., (2015) Safety and Efficacy of Liposome Intraarticular Injection in Moderate Knee Osteoarthritis: A RCT. A poster presented at the American Academy of Orthopaedic Surgeons (AAOS), Mar. 24-28, 2015; Las Vegas, Nevada, USA. 3 pages.
Kawano et al., (2003) Mechanical effects of the intraarticular administration of high molecular weight hyaluronic acid plus phospholipid on synovial joint lubrication and prevention of articular cartilage degeneration in experimental osteoarthritis. Arthritis Rheum 48(7): 1923-1929.
Merkher et al., (2006) A rational human joint friction test using a human cartilage-on-cartilage arrangement. Tribology Letters 22(1): 29-36.
Nitzan et al., (2004) TMJ lubrication system: its effect on the joint function, dysfunction, and treatment approach. Compend Contin Educ Dent 25(6): 437-8, 440, 443-4 passim; quiz 449, 471.
Oloyede et al., (2004) Consolidation responses of delipidized articular cartilage. Clin Biomech (Bristol, Avon) 19(5): 534-542.
Pickard et al., (1998) Investigation into the effects of proteins and lipids on the frictional properties of articular cartilage. 19(19): 1807-1812.
Rinaudo et al., (2014) Effect of Mannitol on Hyaluronic Acid Stability in Two in Vitro Models of Oxidative Stress. Polymers 6(7): 1948-1957.
Sarma et al., (2001) Phospholipid composition of articular cartilage boundary lubricant. J Orthop Res 19(4): 671-676.
Schwarz and Hills (1998) Surface-active phospholipid as the lubricating component of lubricin. Br J Rheumatol 37(1): 21-26.
Sivan et al., (2010) Liposomes act as effective biolubricants for friction reduction in human synovial joints. Langmuir 26(2): 1107-1116.
Talsma et al., (1991) The cryopreservation of liposomes. 1. A differential scanning calorimetry study of the thermal behavior of a liposome dispersion containing mannitol during freezing/thawing. Pharm Res 8(8): 1021-1026.
Thomas et al., (1980) Knee-joint temperature measurement using a differential thermistor thermometer. Rheumatol Rehabil 19(1): 8-13.

(56) References Cited

OTHER PUBLICATIONS

Varjú et al., (2004) Assessment of hand osteoarthritis: correlation between thermographic and radiographic methods. Rheumatology (Oxford) 43(7): 915-919.

Vecchio et al., (1999) Surfactant treatment for osteoarthritis. Rheumatology (Oxford) 38(10): 1020-1021.

Verberne et al., (2010) Liposomes as potential biolubricant additives for wear reduction in human synovial joints. Wear 268(7-8): 1037-1042.

Watanabe et al., (2000) Ultrastructural study of upper surface layer in rat articular cartilage by "in vivo cryotechnique" combined with various treatments. Med Electron Microsc 33(1): 16-24.

Yui et al., (1992) Inflammation responsive degradation of cross-linked hyaluronic acid gels. Journal of Controlled Release 22(2): 105-116.

Conrozier (2018) Is the Addition of a Polyol to Hyaluronic Acid a Significant Advance in the Treatment of Osteoarthritis?. Curr Rheumatol Rev 14(3): 226-230. Abstract.

Conrozier et al., (2014) Mannitol Preserves the Viscoelastic Properties of Hyaluronic Acid in an In Vitro Model of Oxidative Stress. Rheumatol Ther 1: 45-54.

Conrozier et al., (2016) Standardized Follow-up of Patients with Symptomatic Knee Osteoarthritis Treated with a Single Intra-articular Injection of a Combination of Cross-Linked Hyaluronic Acid and Mannitol. Clin Med Insights Arthritis Musculoskelet Disord 9: 175-179.

Dauvissat et al., (2018) Safety and Predictive Factors of Short-Term Efficacy of a Single Injection of Mannitol-Modified Cross-Linked Hyaluronic Acid in Patients with Trapeziometacarpal Osteoarthritis. Results of a Multicentre Prospective Open-Label Pilot Study (INSTINCT Trial). Clin Med Insights Arthritis Musculoskelet Disord 11: 1179544118782901; 7 pages.

Henrotin et al., (2017) Reduction of the Serum Levels of a Specific Biomarker of Cartilage Degradation (Coll2-1) by Hyaluronic Acid (KARTILAGE® CROSS) Compared to Placebo in Painful Knee Osteoarthritis Patients: the EPIKART Study, A Pilot Prospective Comparative Randomized Double Blind Trial. BMC Musculoskelet Disord 18(1): 222; 10 pages.

Lertwanich and Lamsam (2016) Efficacy of a Single Intra-Articular Injection of 2% Sodium Hyaluronate Plus 0.5% Mannitol in Patients with Symptomatic Osteoarthritis of the Knee: A Preliminary Report. J Med Assoc Thai 99(10): 1094-1101.

New Technology for Catalyst Chemical Production. Edited by: Wang Duoren. Scientific and Technical Documents Publishing House, Beijing, China; 1st edition, May 2001. pp. 410-413; with machine translation.

* cited by examiner

LIPOSOMAL FORMULATION FOR JOINT LUBRICATION

FIELD OF THE INVENTION

The present invention relates to liposomal pharmaceutical compositions wherein the phospholipids themselves are the sole active pharmaceutical agents, and their therapeutic use for joint lubrication.

BACKGROUND OF THE INVENTION

Joint dysfunctions affect a very large portion of the population. Sufficient biolubrication is a prerequisite for proper joint mobility, which is crucial for prevention and amelioration of degradative changes of the joint.

A common joint dysfunction is osteoarthritis (OA), with prevalence exceeding 20 million in the United States alone. Current treatment focuses on reducing overloading of joints, physiotherapy, and alleviation of pain and inflammation, usually by systemic or intra-articular administration of drugs.

Articular cartilage forms a smooth, tough, elastic and flexible surface that facilitates bone movement. The synovial space is filled with the highly viscous synovial fluid (SF), containing hyaluronic acid (HA) and the glycoprotein lubricin. HA is a polymer of D-glucuronic acid and D-N-acetylglucosamine, which is highly unstable and degrades under the inflammatory conditions of OA (Nitzan, D. W., Kreiner, B. & Zeltser, R. TMJ lubrication system: its effect on the joint function, dysfunction, and treatment approach. *Compend. Contin. Educ. Dent.* 25, 437-444 (2004); Yui, N., Okano, T. & Sakurai, Y. Inflammation responsive degradation of crosslinked hyaluronic acid gels. *J. Control. Release* 22, 105-116 (1992)). Lubricin is composed of ~44% proteins, ~45% carbohydrates and ~11% phospholipids (PLs), of which ~41% are phosphatidylcholines (PCs), ~27% phosphatidylethanolamines (PEs) and ~32% sphingomyelins. These PLs are referred to as "surface-active phospholipids" (SAPL).

Boundary lubrication, in which layers of lubricant molecules separate opposing surfaces, occurs under loading of articular joints. Several different substances have been proposed as the native boundary lubricants in articular cartilage, including HA and lubricin. Pickard et al. and Schwartz and Hills demonstrated that phospholipids defined as surface active phospholipids of lubricin facilitate joint lubrication in articular cartilage (Pickard, J. E., Fisher, J., Ingham, E. & Egan, J. Investigation into the effects of proteins and lipids on the frictional properties of articular cartilage. *Biomaterials* 19, 1807-1812 (1998); Schwarz, I. M. & Hills, B. A. Surface-active phospholipid as the lubricating component of lubricin. *Br. J. Rheumatol.* 37, 21-26 (1998)). Hills and coworkers demonstrated that OA joints have a SAPL deficiency, and that injection of the surface-active phospholipid 1,2-dipalmitoyl-sn-glycero-3-phosphocholine (DPPC) into joints of OA patients resulted in mobility improvement lasting up to 14 weeks without major side effects (Vecchio, P., Thomas, R. & Hills, B. A. Surfactant treatment for osteoarthritis. *Rheumatology (Oxford)* 38, 1020-1021 (1999); Gudimelta, O. A., Crawford, R. & Hills, B. A. Consolidation responses of delipidized cartilage. *Clin. Biomech.* 19, 534-542 (2004)). In another study, utilizing a unique cryogenic cartilage preservation technique, Watanabe et al. observed lipidic globular vesicles on the surface of healthy cartilage, which are assumed to play a major role in lubrication (Watanabe, M. et al. Ultrastructural study of upper surface layer in rat articular cartilage by "in vivo cryotechnique" combined with various treatments. *Med. Elect. Microsc.* 33, 16-24 (2000)). Kawano et al. and Forsey et al., using animal models, have shown that use of high molecular weight HA (~2000 kDa) combined with DPPC improved lubricating ability of the latter (Kawano, T. et al. Mechanical effects of the intraarticular administration of high molecular weight hyaluronic acid plus phospholipid on synovial joint lubrication and prevention of articular cartilage degeneration in experimental osteoarthritis. *Arthritis Rheum.* 48, 1923-1929 (2003); Forsey, R. W. et al. The effect of hyaluronic acid and phospholipid based lubricants on friction within a human cartilage damage model. *Biomaterials* 27, 4581-4590 (2006)).

U.S. Pat. No. 6,800,298 discloses dextran-based hydrogel compositions containing lipids, particularly phospholipids, for lubrication of mammalian joints.

US Patent Application 2005/0123593 is directed to a composition comprising glycosaminoglycans encapsulated in a liposomal delivery system for intraarticular administration for the treatment of osteoarthritis.

U.S. Pat. No. 8,895,054 concerns methods of joint lubrication and/or prevention of cartilage wear making use of liposomes consisting essentially of phospholipid membranes having a phase transition temperature in the range of about 20° C. to about 39° C.

Commercially available pharmaceutical compositions for the prevention and treatment of osteoarthritis, which are based on hyaluronic acid as an active ingredient, include, inter alia, Antalvisc®, Kartilage® and Kartilage® Cross. Said pharmaceutical compositions include mannitol in addition to HA. It was found that mannitol has an ability to reduce HA degradation under oxidative stress and therefore can be used to significantly increase the intra-articular residence time of the injected HA and improve viscosupplementation effectiveness of HA-based intra-articular injections (M. Rinaudo, B. Lardy, L. Grange, and T. Conrozier, *Polymers* 2014, 6, 1948-1957). A clinical study comparing both safety and efficacy of an intra-articular viscosupplement made of intermediate molecular weight (MW) hyaluronic acid mixed with high concentration of mannitol and a high MW HA alone (Bio-HA), in patients with knee osteoarthritis revealed that the mannitol-containing viscosupplement was not less effective than its comparator Bio-HA, in terms of pain relief and function improvement over six months, without inducing more side effects (Conrozier, Thierry et al. *The Knee,* 2016, 23 (5), 842-848). The effect of mannitol on the efficacy of HA-based viscosupplement compositions was also studied by Eymard et al., (Eymard F, Bossert M, Lecurieux R, Maillet B, Chevalier X, et al. (2016) Addition of Mannitol to Hyaluronic Acid may Shorten Viscosupplementation Onset of Action in Patients with Knee Osteoarthritis: Post-Hoc Analysis of A Double-blind, Controlled Trial. J Clin Exp Orthop 2: 21) and Conrozier, T. et al. (Role of high concentrations of mannitol on the stability of hyaluronan in an oxidative stress model induced by xanthine/xanthine oxidase Osteoarthritis and Cartilage, Volume 22, S478). Ferraccioli et al. have showed that ultra-violet illumination of synovial fluid could be a helpful method for the screening of the free radical scavenging effect of drugs, as it induces a viscosity fall due to the production of free radicals. The protection of the viscosity of human synovial fluid was mediated by Superoxide dismutase, mannitol and catalase (G. F. Ferraccioli, U. Ambanelli, P. Fietta, N. Giudicelli, C. Giori, Decrease of osteoarthritic synovial fluid viscosity by means of u.v.

illumination: A method to evaluate the free radical scavenging action of drugs, Biochemical Pharmacology, 30, (13) 1981, 1805-1808).

International Patent Application WO2012/001679 is directed to an injectable pharmaceutical formulation for the alleviation or reduction of joint irritation or for the reduction of worsening of existing joint inflammation, formulated for intra-articular injection, comprising an active polyol ingredient, which polyol active ingredient is xylitol. The efficacy of xylitol was compared with the efficacy of mannitol and glycerol for the prevention of joint irritation, and it was disclosed that a solution of mannitol or glycerol did not prevent irritation, when injected by intra-articular injection into a rabbit's knee.

US Patent Application 2014/0038917 is directed to a sterile and injectable aqueous formulation for administration in the intra-articular space of an intra-articular joint of a subject, in the form of a gel comprising: hyaluronic acid, or one of its salts, and a polyol, preferably, sorbitol at a concentration equal or higher than 7 mg/ml.

International Patent Application WO2003/000191 relates to a composition and method for treating arthritis comprising one or more glycosaminoglycans in combination with one or more hyaluronidase inhibitors, wherein the hyaluronidase inhibitors can be selected from heparan sulphate, dextran sulphate and xylose sulphate, and wherein hyaluronic acid can be co-encapsulated with a hyaluronidase inhibitor in liposomes.

Injectable HA compositions are known to have various side effects, such as difficulty with moving, muscle pain or stiffness, pain in the joints and swelling or redness in the joint. Some of the side effects of Antalvisc® include transient pain and swelling of the injected joint following injection.

There remains, therefore, an unmet need for an efficient pharmaceutical composition for joint lubrication, which would provide a long-lasting effect, while reducing the probability of side effects associated with intra-articular administration.

SUMMARY OF THE INVENTION

The present invention provides a liposomal formulation for introduction into synovial joints to provide lubrication in order to reduce pain and irritation and improve or restore joint mobility. The liposomal formulation is adapted specifically for intra-articular delivery. The pharmaceutical composition of the present invention comprises liposomes, as an active ingredient, which comprise phospholipid membranes having a phase transition temperature which is slightly lower than the physiological temperature. The liposomes are therefore in the liquid-disordered (LD) phase when administered to the synovial joint. The pharmaceutical composition further comprises a tonicity agent which is a polyol. The tonicity agent is being used to reduce local irritation by preventing osmotic shock at the site of application.

The present invention is based in part on the surprising discovery that non-ionic tonicity agents, which were added to the liposomal composition, provided enhanced lubrication as compared to an ionic tonicity agent. In particular, addition of mannitol to the liposomal formulation improved the lubrication efficacy of the composition, whereas the use of sodium chloride resulted in decreased lubrication efficiency of the liposomes. The effect of mannitol is even more surprising in view of the fact that the pharmaceutical compositions do not comprise any additional pharmaceutically active agent besides the phospholipids themselves, and in particular, do not contain hyaluronic acid, the activity of which is known to be enhanced by the addition of polyols. Addition of a different non-ionic polyol, including specifically glycerol, also resulted in enhancement of the lubrication ability of the liposomal formulation, as compared to the use of sodium chloride, though to a less pronounced extent.

Thus, in accordance with a first aspect, the present invention provides a pharmaceutical composition comprising a tonicity agent, comprising a polyol; and liposomes comprising at least one membrane comprising at least one phospholipid (PL) selected from a glycerophospholipid (GPL), said GPL having two $C_{12}$-$C_{18}$ hydrocarbon chains, being the same or different, and sphingomyelin (SM) having a $C_{12}$-$C_{18}$ hydrocarbon chain, wherein the at least one membrane has a phase transition temperature in the range of about 20° C. to about 39° C.; wherein the pharmaceutical composition is essentially free of an additional pharmaceutically active agent. The pharmaceutical composition is useful in the lubrication of a mammalian joint having a temperature which is above the phase transition temperature. According to some embodiments, the tonicity agent is non-ionic. According to further embodiments, the polyol is selected from mannitol and glycerol. According to a specific embodiment, the tonicity agent comprises mannitol.

In another aspect there is provided a method for lubricating a joint of a mammal, the method comprising: administering into a cavity of the joint a pharmaceutical composition comprising a tonicity agent, comprising a polyol; and liposomes comprising at least one membrane comprising at least one phospholipid (PL) selected from a glycerophospholipid (GPL), said GPL having two $C_{12}$-$C_{18}$ hydrocarbon chains, being the same or different, and sphingomyelin (SM) having a $C_{12}$-$C_{18}$ hydrocarbon chain, wherein the at least one membrane has a phase transition temperature in the range of about 20° C. to about 39° C.; wherein the pharmaceutical composition is essentially free of an additional pharmaceutically active agent, wherein the joint has a joint temperature which is above the phase transition temperature. According to some embodiments, the tonicity agent is non-ionic. According to further embodiments, the polyol is selected from mannitol and glycerol. According to a specific embodiment, the tonicity agent comprises mannitol.

In another aspect there is provided a method for the treatment of pain or irritation in a joint of a subject having an articular disorder, the method comprising lubricating a joint of said subject by administering into a cavity of the joint a pharmaceutical composition comprising a tonicity agent comprising a polyol; and liposomes comprising at least one membrane comprising at least one phospholipid (PL) selected from a glycerophospholipid (GPL), said GPL having two $C_{12}$-$C_{18}$ hydrocarbon chains, being the same or different, and sphingomyelin (SM) having a $C_{12}$-$C_{18}$ hydrocarbon chain, wherein the at least one membrane has a phase transition temperature in the range of about 20° C. to about 39° C.; wherein the pharmaceutical composition is essentially free of an additional pharmaceutically active agent, and wherein the joint has a joint temperature which is above the phase transition temperature. According to some embodiments, the tonicity agent is non-ionic. According to further embodiments, the polyol is selected from mannitol and glycerol. According to a specific embodiment, the tonicity agent comprises mannitol.

In another aspect, the invention provides the use of a tonicity agent, comprising a polyol; and liposomes consisting essentially of at least one membrane comprising at least one phospholipid (PL) selected from a glycerophospholipid (GPL), said GPL having two $C_{12}$-$C_{18}$ hydrocarbon chains, being the same or different, and sphingomyelin (SM) having a $C_{12}$-$C_{18}$ hydrocarbon chain, wherein the at least one membrane has a phase transition temperature in the range of about 20° C. to about 39° C., for the preparation of a pharmaceutical composition for lubrication of a mammalian joint having a temperature above said phase transition temperature, wherein the pharmaceutical composition is essentially free of an additional pharmaceutically active agent. According to some embodiments, the tonicity agent is non-ionic. According to further embodiments, the polyol is selected from mannitol and glycerol. According to a specific embodiment, the tonicity agent comprises mannitol.

In some embodiments, the polyol does not include xylitol.

In some embodiments, the polyol is present in the pharmaceutical composition in a weight percent ranging from about 5% (w/w) to about 50% (w/w) of the dry weight of the pharmaceutical composition. In some embodiments, mannitol is present in the pharmaceutical composition in a weight percent ranging from about 20% (w/w) to about 40% (w/w) of the dry weight of the pharmaceutical composition. In some embodiments, glycerol is present in the pharmaceutical composition in a weight percent ranging from about 5% (w/w) to about 25% (w/w) of the dry weight of the pharmaceutical composition. In some embodiments, the phospholipids are present in the pharmaceutical composition in a weight percent ranging from about 50% (w/w) to about 95% (w/w) of the dry weight of the pharmaceutical composition.

In some embodiments, the pharmaceutical composition further comprises a fluid medium in which the liposomes are dispersed or suspended. In further embodiments, the polyol is dispersed or dissolved in said fluid medium. In still further embodiments, mannitol is dissolved in said fluid medium. The fluid medium can be selected from buffer and water. In certain embodiments, said buffer comprises a histidine buffer or phosphate buffered saline. Each possibility represents a separate embodiment of the invention. In certain embodiments, said buffer comprises a histidine buffer.

In some embodiments, the pharmaceutical composition is in the form of a pharmaceutically acceptable suspension comprising liposomes suspended in the fluid medium.

According to some embodiments, the concentration of the polyol inside the liposome is essentially the same as the concentration of the polyol in the medium outside the liposome.

In some embodiments, the polyol is present in the pharmaceutical composition in a weight percent ranging from about 0.05% (w/w) to about 10% (w/w) of the total weight of the pharmaceutical composition. In further embodiments, the weight percent of the polyol ranges from about 0.1% (w/w) to about 7% (w/w). In still further embodiments, the weight percent of the polyol ranges from about 1% (w/w) to about 5% (w/w).

In some embodiments, mannitol is present in the pharmaceutical composition in a weight percent ranging from about 0.1% (w/w) to about 7% (w/w) of the total weight of the pharmaceutical composition. In further embodiments, the weight percent of mannitol ranges from about 1% (w/w) to about 7% (w/w).

In some embodiments, glycerol is present in the pharmaceutical composition in a weight percent ranging from about 0.05% (w/w) to about 5% (w/w) of the total weight of the pharmaceutical composition. In further embodiments, the weight percent of glycerol ranges from about 0.5% (w/w) to about 5% (w/w).

In some embodiments, the pharmaceutical composition has osmolality in the range from about 200 to about 600 mOsm. In certain embodiments, the pharmaceutical composition has osmolality of about 300 mOsm. In certain such embodiments, the pharmaceutical composition is isotonic.

In some embodiments, the pharmaceutical composition has a pH of about 5-8.

In some embodiments, the weight ratio between the liposomes and the polyol ranges from about 15:1 to about 1:1. In further embodiments, the weight ratio between the liposomes and mannitol ranges from about 10:1 to about 1:1. In additional embodiments, the weight ratio between the liposomes and glycerol ranges from about 15:1 to about 2:1.

According to some embodiments, the liposomes have more than one membrane. In certain such embodiments, the liposomes are multilamellar vesicles (MLV).

In some embodiments, the GPL comprises two acyl chains. In further embodiments, said chains are selected from the group consisting of $C_{14}$, $C_{15}$, $C_{16}$ and $C_{18}$ acyl chains. In certain embodiments, at least one of said hydrocarbon chains is a saturated hydrocarbon chain. In further embodiments, the two hydrocarbon chains are saturated.

In some embodiments, the PL is a phosphatidylcholine (PC). In further embodiments, the at least one membrane comprises 1,2-dimyristoyl-sn-glycero-3-phosphocholine (DMPC).

In some embodiments, the at least one membrane further comprises a PC selected from the group consisting of 1,2-dipalmitoyl-sn-glycero-3-phosphocholine (DPPC), 1,2-dipentadecanoyl-sn-glycero-3-phosphocholine (C15), 1,2-distearoyl-sn-glycero-3-phosphocholine (DSPC), and N-palmitoyl-D-erythro-sphingosylphosphorylcholine (D-erythro C16). In some embodiments, the mole percent of DMPC in the at least one membrane ranges from about 10% to about 75%.

In some embodiments, the at least one membrane comprises DMPC and DPPC. In further embodiments, the mole percent ratio of DMPC to DPPC is in the range of about 25:75 to about 70:30. In certain embodiments, the mole percent ratio of DMPC to DPPC is about 45:55.

In some embodiments, the at least one membrane comprises DMPC and C15. In further embodiments, the mole percent ratio of DMPC to C15 is in the range of about 25:75 to about 45:55.

In some embodiments, the at least one membrane comprises DMPC and DSPC. In further embodiments, the mole percent ratio of DMPC to DSPC is about 75:25.

In some embodiments, the at least one membrane comprises DMPC and D-erythro C16. In further embodiments, the mole percent ratio of DMPC to D-erythro C16 is in the range of about 10:90 to about 25:75.

In some embodiments, the at least one membrane comprises C15.

The total concentration of the phospholipids in the pharmaceutical composition according to some embodiments of the invention ranges from about 50 to about 300 mM. In certain embodiments, the total concentration of the phospholipids ranges from about 100 mM to about 200 mM.

In some embodiments, the phospholipids are present in the pharmaceutical composition in a weight percent ranging from about 0.5% (w/w) to about 30% (w/w) of the total weight of the pharmaceutical composition. In further embodiments, the weight percent of the phospholipids ranges from about 3% (w/w) to about 30% (w/w).

In some embodiments, the liposomes have a mean diameter of between about 0.5 µm to about 10 µm.

In certain embodiments, the at least one membrane has the phase transition temperature of about 30° C. to about 35° C.

In some embodiments, the temperature of the joint is in the range of about 1-15° C. above said phase transition temperature.

In some currently preferred embodiments, the pharmaceutical composition is being essentially free of hyaluronic acid.

In certain embodiments, the liposomes consist essentially of the at least one membrane comprising at least one phospholipid (PL), as detailed hereinabove.

In some embodiments, the pharmaceutical composition comprises MLV liposomes which membranes consist essentially of DMPC and DPPC; mannitol; and histidine buffer. In further embodiments, DMPC is present in the pharmaceutical composition in a weight percent ranging from about 1% (w/w) to about 10% (w/w) of the total weight of the pharmaceutical composition. In still further embodiments, DPPC is present in the pharmaceutical composition in a weight percent ranging from about 2% (w/w) to about 12% (w/w) of the total weight of the pharmaceutical composition. In yet further embodiments, mannitol is present in the pharmaceutical composition in a weight percent ranging from about 1% (w/w) to about 7% (w/w) of the total weight of the pharmaceutical composition.

In some embodiments, the lubrication of the joint is for the treatment of an articular disorder or symptoms arising therefrom. In further embodiments, the articular disorder is selected from the group consisting of arthritis, osteoarthritis, osteoarthritis in rheumatoid arthritis patients, traumatic joint injury, locked joint, sports injury, status post arthrocentesis, arthroscopic surgery, open joint surgery, and joint replacement. Each possibility represents a separate embodiment of the invention. In certain embodiments, the pharmaceutical composition is for the reduction of knee joint pain in osteoarthritis patients.

In some embodiments, the lubrication is for preventing joint wear.

According to specific embodiments the pharmaceutical composition is a parenteral pharmaceutical composition comprising a suspension of liposomes. The pharmaceutical composition can be in a form suitable for administration by intra-articular injection, arthroscopic administration or by surgical administration. Each possibility represents a separate embodiment of the invention.

The pharmaceutical composition according to the various embodiments of the invention may be administered in a dose of from about 0.5 ml to about 10 ml. In further embodiments, the pharmaceutical composition is administered in a dose of from about 1 ml to about 6 ml. In certain embodiments, the pharmaceutical composition is administered in a dose of about 3 ml.

In some embodiments, one dosage unit of the pharmaceutical composition comprises from about 20 mg to about 350 mg mannitol. In a certain embodiment, one dosage unit of the pharmaceutical composition comprises about 120 mg mannitol.

In some embodiments, one dosage unit of the pharmaceutical composition comprises from about 50 mg to about 1000 mg phospholipids. In some embodiments, one dosage unit of the pharmaceutical composition comprises from about 50 mg to about 500 mg DPPC. In some embodiments, one dosage unit of the pharmaceutical composition comprises from about 40 mg to about 300 mg DMPC.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF SOME EMBODIMENTS

Figure 1:
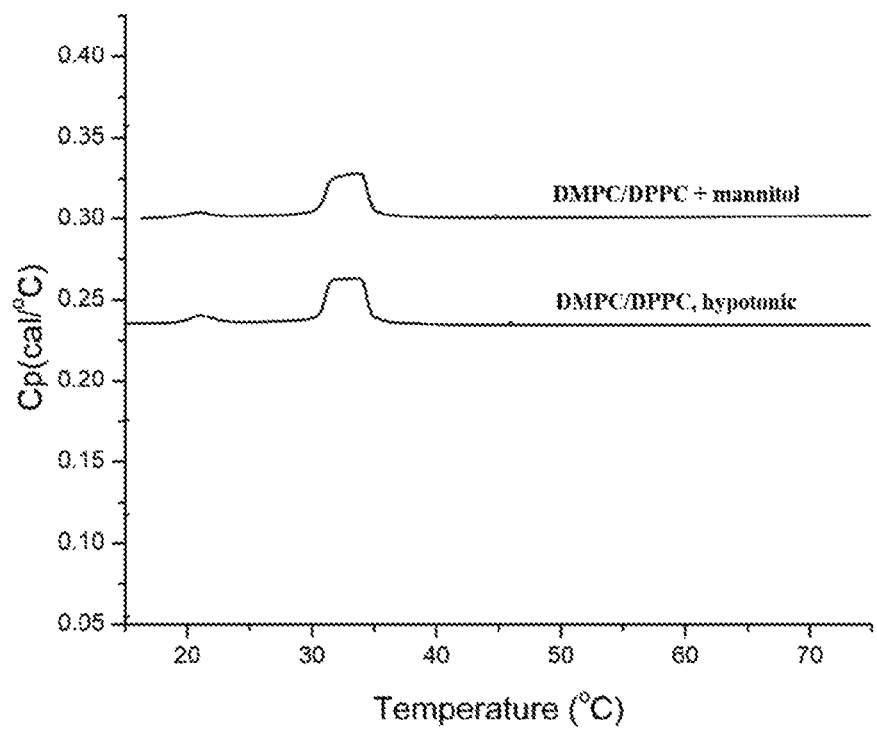
FIG. 1 shows raw Differential Scanning calorimetry (DSC) thermograms of isotonic and hypotonic liposomal compositions comprising DMPC/DPPC.

The present invention provides a liposomal formulation for use in the lubrication of mammalian joints, said lubrication providing reduced pain and irritation and allowing to improve or restore joint mobility and reduce wear of the joint. The pharmaceutical composition can further be used for the treatment, management or prevention of an articular disorder or condition. The pharmaceutical composition according to the principles of the invention is based on a liposomal composition, having a defined phase transition temperature of the liposomes' membranes, said temperature being below the temperature of the joint.

The term "phase transition temperature", as used herein, refers in some embodiments, to a temperature at which solid ordered (SO) to liquid disordered (LD) phase transition of the liposome occurs. The phase transition temperature of the liposomes can be evaluated by Differential Scanning calorimetry (DSC). Various parameters of the DSC thermogram which can be examined to assess the phase transition temperature include $T_{on}$, which represents the temperature at which the SO-LD phase transition is initiated and $T_{off}$ which represents the temperature at which the SO-LD phase transition ends during heating scans, and $T_p$, and $T_m$, which represent the temperature at which the maximum change in the heat capacity during the pre-transition ($T_p$) and main transition ($T_m$) occurs, respectively.

Multilamellar vesicle liposomes composed of various PCs, with two $C_{12}$-C16 hydrocarbon chains where previously shown to be effective cartilage lubricants and wear reducers at temperature slightly above (e.g. about 1° C., 2° C., 3° C., 5° C., 8° C., 11° C. and at times up to about 15° C.) the SO-to-LD phase transition temperature (as detailed in the U.S. Pat. No. 8,895,054, the contents of which is hereby incorporated by reference in its entirety). Pharmaceutical compositions of the present invention further comprise a non-ionic tonicity agent, which increases osmolarity of the composition.

It was surprisingly found that lubrication efficiency of the pharmaceutical composition comprising a non-ionic polyol was significantly higher as compared to a pharmaceutical composition comprising an ionic tonicity agent, and in particular, sodium chloride salt. The positive effect of the polyols as compared to sodium chloride was entirely unforeseen, since the pharmaceutical composition of the invention is not based on hyaluronic acid, activity of which is known to be enhanced by the addition of polyols.

The inventors have further shown that the addition of mannitol did not alter the phase transition temperature of the liposome membranes. Without wishing to being bound by theory or mechanism of action, it can be assumed that the surprising effect of the polyol addition is not directly related to the phase transition temperature of the liposome, which has been previously reported to be the essential feature affording for the lubrication ability thereof.

Thus, in accordance with an aspect of the invention, there is provided a pharmaceutical composition comprising a tonicity agent, comprising a polyol; and a liposome comprising at least one phospholipid (PL) selected from glycerophospholipid (GPL) or sphingolipid (SPL) and having a phase transition temperature in the range of about 20° C. to about 39° C., wherein the pharmaceutical composition is essentially free of an additional pharmaceutically active agent. In some embodiments, the pharmaceutical composition is for use in the lubrication of a mammalian joint.

In another aspect, there is provided a method for lubricating a joint of a mammal, the method comprising: administering into a cavity of the joint a pharmaceutical composition comprising: a tonicity agent, comprising a polyol; and a liposome comprising at least one phospholipid (PL) selected from glycerophospholipid (GPL) or sphingolipid (SPL) having a phase transition temperature in the range of about 20° C. to about 39° C., wherein the pharmaceutical composition is essentially free of an additional pharmaceutically active agent.

In another aspect there is provided a method for the treatment of pain or irritation in a joint of a subject having an articular disorder, the method comprising lubricating a joint of said subject by administering into a cavity of the joint a pharmaceutical composition comprising: a tonicity agent, comprising a polyol; and a liposome comprising at least one phospholipid (PL) selected from glycerophospholipid (GPL) or sphingolipid (SPL) having a phase transition temperature in the range of about 20° C. to about 39° C., wherein the pharmaceutical composition is essentially free of an additional pharmaceutically active agent.

In another aspect, the invention provides the use of a tonicity agent, comprising a polyol and a liposome comprising at least one phospholipid (PL) selected from glycerophospholipid (GPL) or sphingolipid (SPL) having a phase transition temperature in the range of about 20° C. to about 39° C., for the preparation of a pharmaceutical composition for lubrication of a mammalian joint, wherein the pharmaceutical composition is essentially free of an additional pharmaceutically active agent.

The term "tonicity agent", as used herein, refers in some embodiments to a tonicity agent suitable for use in pharmaceutical compositions for intra-articular injection.

In some embodiments, the tonicity agent is non-ionic. In some embodiments, the polyol is a linear polyol. In some embodiments, the polyol is a cyclic polyol. Non-limiting examples of non-ionic polyols suitable for use in the pharmaceutical composition of the invention include mannitol, glycerol, dextrose, lactose, and trehalose.

In some currently preferred embodiments, the polyol is mannitol. Mannitol is a well-known and low-cost excipient, frequently used by formulators in various types of pharmaceutical compositions. As mentioned hereinabove, mannitol has been used in combination with hyaluronic acid in pharmaceutical compositions for joint lubrication. Mannitol has also been reported as being useful in cryopreservation of liposomes (Talsma H, van Steenbergen M J, Salemink P J, Crommelin D J, Pharm Res. 1991, 8 (8):1021-6).

In some embodiments, the tonicity agent comprises glycerol.

In some embodiments, the pharmaceutical composition comprises a combination of polyols, i.e., a combination of mannitol and glycerol. The pharmaceutical composition can further include a combination of a polyol with an additional tonicity agent.

In some embodiments, the polyol does not include xylitol.

It is to be emphasized that according to some currently preferred embodiments, the tonicity agent is not encapsulated within the liposomes. The term "encapsulated", as used herein, refers in some embodiments, to the concentration of the tonicity agent inside the liposome being substantially higher than in the medium outside the liposome. The term "inside the liposome" is to be understood as encompassing at least one inner aqueous phase of the liposome. The term "concentration" can include osmotic concentration. The term "substantially higher", as used herein, refers in some embodiments to the difference in the concentration of at least about 90%. In some embodiments, the polyol is not encapsulated within the liposomes. In further embodiments, mannitol is not encapsulated within the liposomes. In additional embodiments, glycerol is not encapsulated within the liposomes.

According to further embodiments, the concentration of the tonicity agent inside the liposome is essentially the same as the concentration of the tonicity agent in the medium outside the liposome. The term "essentially the same", as used herein, refers in some embodiments, to the difference in the concentration of less than about 15%. In further embodiments, the term "essentially the same" refers to the difference in the concentration of less than about 10%, less than about 5%, less than about 2.5%, or less than about 1%. Each possibility represents a separate embodiment of the invention.

According to further embodiments, the concentration of the polyol inside the liposome is essentially the same as the concentration of the polyol in the medium outside the liposome. According to still further embodiments, the concentration of mannitol inside the liposome is essentially the same as the concentration of mannitol in the medium outside the liposome. According to yet further embodiments, the concentration of the glycerol inside the liposome is essentially the same as the concentration of glycerol in the medium outside the liposome.

In some embodiments, the liposomes are not freeze-dried. In further embodiments, the liposomes are not freeze-dried and/or thawed prior to the administration to the joint.

In some embodiments, the pharmaceutical composition further comprises a fluid medium. In some embodiments, the liposomes are dispersed or suspended in said fluid medium. In further embodiments the tonicity agent is dissolved or dispersed in said fluid medium. In further embodiments, mannitol or glycerol are dissolved in said fluid medium. In some embodiments, the pharmaceutical composition is in a form of a pharmaceutically acceptable suspension comprising liposomes suspended in the fluid medium.

Further provided is a pharmaceutically acceptable suspension comprising the pharmaceutical composition according to the various embodiments hereinabove and further comprising a fluid medium.

In some embodiments, the polyol is present in the pharmaceutical composition in a weight percent ranging from about 5% (w/w) to about 50% (w/w), or from about 10% (w/w) to about 40% (w/w) of the dry weight of the pharmaceutical composition. In certain embodiments, the polyol is present in the pharmaceutical composition in a weight percent of about 30% (w/w) of the dry weight of the pharmaceutical composition. In additional embodiments, the polyol is present in the pharmaceutical composition in a weight percent of about 15% (w/w) of the dry weight of the pharmaceutical composition.

In some embodiments, mannitol is present in the pharmaceutical composition in a weight percent ranging from about 10% (w/w) to about 50% (w/w), or from about 20% (w/w) to about 50% (w/w) of the dry weight of the pharmaceutical composition. In further embodiments, mannitol is present in the pharmaceutical composition in a weight percent of about 30% (w/w) of the dry weight of the pharmaceutical composition.

In some embodiments, glycerol is present in the pharmaceutical composition in a weight percent ranging from about 5% (w/w) to about 35% (w/w), or from about 5% (w/w) to about 25% (w/w) of the dry weight of the pharmaceutical composition. In further embodiments, glycerol is present in the pharmaceutical composition in a weight percent of about 15% (w/w) of the dry weight of the pharmaceutical composition.

In some embodiments, the phospholipids forming the liposomes are present in the pharmaceutical composition in a weight percent ranging from about 50% (w/w) to about 95% (w/w), or from about 60% (w/w) to about 85% (w/w) of the dry weight of the pharmaceutical composition. In further embodiments, the phospholipids are present in the pharmaceutical composition in a weight percent of about 70% (w/w) of the dry weight of the pharmaceutical composition. In further embodiments, the phospholipids are present in the pharmaceutical composition in a weight percent of about 85% (w/w) of the dry weight of the pharmaceutical composition.

The term "dry weight", as used herein, refers in some embodiments, to the weight of a pharmaceutical composition, which does not include a fluid medium. In further embodiments, the term "dry weight" refers to the weight of a pharmaceutical composition, which does not include water.

In some embodiments, the compositions of this invention are pharmaceutically acceptable. The term "pharmaceutically acceptable", as used herein, refers in some embodiments to any formulation which is safe, and provides the appropriate delivery for the desired route of administration of an effective amount of the active ingredient for use in the present invention. This term refers to the use of buffered formulations as well, wherein the pH is maintained at a particular desired value, ranging from pH 4.0 to pH 9.0, in accordance with the stability of the compounds and route of administration.

The fluid medium can be, therefore, selected from buffer, water, and salt solution. In some embodiments, the fluid medium comprises buffer. In certain embodiments, said buffer comprises a histidine buffer or phosphate buffered saline. Each possibility represents a separate embodiment of the invention. The concentration of histidine can range from about 0.5 mg/ml to about 10 mg/ml. In certain embodiments, the concentration of histidine is about 2 mg/ml. In some embodiments, the concentration of histidine ranges from about 1 mM to about 50 mM. In certain embodiments, the concentration of histidine is about 10 mM. Histidine can be present in the composition in the form of a dissolved hydrochloric or acetate salt. In certain embodiments, the pharmaceutical composition further comprises trace amounts of inorganic acids, such as, for example, hydrochloric acid.

The pH of the pharmaceutical composition can range between about 5 to about 8. In some embodiments, the pH ranges between about 6 and about 7. In certain embodiments, the pH of the pharmaceutical composition is about 6.5.

In some embodiments, the concentration of the polyol in the pharmaceutical composition ranges from about 0.5 to about 100 mg/ml. In further embodiments, the concentration of the polyol ranges from about 1 to about 70 mg/ml. In still further embodiments, the concentration of the polyol ranges from about 2.5 to about 60 mg/ml. In yet further embodiments, the concentration of the polyol ranges from about 5 to about 50 mg/ml. In still further embodiments, the concentration of the polyol ranges from about 30 to about 50 mg/ml. In certain embodiments, the concentration of the polyol ranges from about 5 to about 30 mg/ml.

In some embodiments, the concentration of mannitol in the pharmaceutical composition ranges from about 1 mg/ml to about 70 mg/ml. In further embodiments, the concentration of mannitol ranges from about 10 mg/ml to about 70 mg/ml. In still further embodiments, the concentration of mannitol ranges from about 10 mg/ml to about 50 mg/ml. In certain embodiments, the concentration of mannitol is about 40 mg/ml. In additional embodiments, the concentration of mannitol is about 20 mg/ml.

In some embodiments, the concentration of glycerol in the pharmaceutical composition ranges from about 0.5 mg/ml to about 50 mg/ml. In further embodiments, the concentration of glycerol ranges from about 1 mg/ml to about 40 mg/ml. In still further embodiments, the concentration of glycerol ranges from about 5 mg/ml to about 30 mg/ml. In certain embodiments, the concentration of glycerol is about 20 mg/ml. In additional embodiments, the concentration of glycerol is about 10 mg/ml.

In some embodiments, the concentration of polyol in the pharmaceutical composition ranges from about 50 to about 500 mM. In further embodiments, the concentration of polyol ranges from about 100 to about 400 mM. In still further embodiments, the concentration of polyol ranges from about 200 to about 300 mM. The polyol can be selected from mannitol and glycerol.

In some embodiments, the polyol is present in the pharmaceutical composition in a weight percent ranging from about 0.05% (w/w) to about 10% (w/w), from about 0.1% (w/w) to about 7% (w/w), from about 0.5% (w/w) to about 10% (w/w), or from about 1% (w/w) to about 5% (w/w) of the total weight of the pharmaceutical composition. In certain embodiments, the weight percent of the polyol is about 4% (w/w). In additional embodiments, the weight percent of the polyol is about 2% (w/w).

In some embodiments, mannitol is present in the pharmaceutical composition in a weight percent ranging from about 0.1% (w/w) to about 7% (w/w), from about 0.5% (w/w) to about 10% (w/w), or from about 1% (w/w) to about 7% (w/w) of the total weight of the pharmaceutical composition. In certain embodiments, the weight percent of mannitol is about 4% (w/w).

In some embodiments, glycerol is present in the pharmaceutical composition in a weight percent ranging from about 0.05% (w/w) to about 5% (w/w), or from about 0.5% (w/w) to about 5% (w/w) of the total weight of the pharmaceutical composition. In certain embodiments, the weight percent of glycerol is about 2% (w/w).

The term "total weight", as used herein, refers in some embodiments to the weight of the pharmaceutical composition comprising the fluid medium. In further embodiments, the term "total weight" refers to the weight of the pharmaceutically acceptable suspension.

In some embodiments, the pharmaceutical composition has osmolality in the range from about 200 to about 600 mOsm. In further embodiments, the pharmaceutical composition has osmolality in the range from about 250 to about 500 mOsm. In further embodiments, the pharmaceutical composition has osmolality in the range from about 250 to about 400 mOsm. In certain embodiments, the pharmaceutical composition has osmolality of about 300 mOsm. In certain such embodiments, the pharmaceutical composition is isotonic.

In some embodiments, the weight ratio between the liposomes and the polyol ranges from about 30:1 to about 1:2. In further embodiments, the weight ratio between the liposomes and the polyol ranges from about 15:1 to about 2:1. In still further embodiments, the weight ratio between the liposomes and the polyol ranges from about 10:1 to about 2:1. In yet further embodiments, the weight ratio between the liposomes and the polyol ranges from about 6:1 to about 2:1. In additional embodiments, the weight ratio between the liposomes and the polyol ranges from about 10:1 to about 6:1

In some embodiments, the weight ratio between the liposomes and mannitol ranges from about 10:1 to about 1:1. In further embodiments, the weight ratio between the liposomes and mannitol ranges from about 6:1 to about 2:1. In certain embodiments, the weight ratio between the liposomes and mannitol is about 4:1.

In some embodiments, the weight ratio between the liposomes and glycerol ranges from about 15:1 to about 2:1. In further embodiments, the weight ratio between the liposomes and glycerol ranges from about 12:1 to about 2:1. In still further embodiments, the weight ratio between the liposomes and glycerol ranges from about 10:1 to about 6:1.

In some embodiments, the pH of the pharmaceutical composition can be adjusted by the use of an inorganic acid or base. The non-limiting examples of suitable inorganic bases include sodium hydroxide and potassium hydroxide. Each possibility represents a separate embodiment of the invention.

In accordance with some embodiments of the invention, the GPL comprises a phosphocholine headgroup (phosphatidylcholine, PC-based lipid) or a phosphoglycerol headgroup (phosphatidylglycerol, PG-based lipid), and the SPL is a ceramide (N-acyl sphingosine carrying a phosphocholine headgroup, also referred to as N-acyl sphingosine-phosphocholine (SM-based lipid).

PCs and SMs are zwitterionic phospholipids with cationic choline and anionic diester phosphate moieties (constituting the phosphocholine head group). The hydrophobic part of the PC and PG includes 2 hydrocarbon (e.g. acyls and alkyls) chains. The SM also has two hydrophobic hydrocarbon chains of which one is the chain of the sphingoid base itself and the other is N-acyl chain. PC, SM and PG in which the hydrocarbon chains is above 12 carbon atoms are all cylinder like in shape as their packing parameter is in the range of 0.74-1.0. They form lipid bilayers which become highly hydrated and vesiculate to form lipid vesicles (liposomes) above the SO to LD phase transition temperature. The PC and PG liposome bilayers can be either in a solid ordered (SO) phase, or in a liquid disordered (LD). The transformation between the SO to LD phases involves an endothermic, first order phase transition referred to as the main phase transition. $T_m$ is the temperature in which the maximum change in the heat capacity change during the SO to LD phase transition occurs. $T_m$ and the temperature range of the SO to LD phase transition of PLs depend, inter alia, on PL hydrocarbon chain composition. In the LD phase (but not in the SO phase), the charged phosphocholine and phosphoglycerol head group are highly hydrated.

In some embodiments, the term "phase transition temperature" refers to the $T_m$. In other embodiments, the term "phase transition temperature" refers the temperature range of the SO to LD phase transition.

It is further noted that PGs and SM have $T_m$ that are similar to that of the corresponding PC (the same length of substituting hydrocarbon chain(s)). For instance, the $T_m$ of 1,2-dimyristoyl-sn-glycero-3-phosphorylglycerol (DMPG) is identical to that of DMPC, namely, 23° C., and that of 1,2-dipalmitoyl-sn-glycero-3-phosphorylglycerol (DPPG) or N-palmitoyl SM is identical to that of DPPC, namely, 41° C. Thus, while the following examples make use mainly of PC-based lipids, the PL in accordance with the invention may also be a PG- or SM-based lipid.

In accordance with the principles of the invention, a mixture of two or more PLs (e.g. two different PCs, a PC with PG, two different PGs, two SM, a PC or PG with SM, etc.) may be used, as long as the mixture formed is in a LD state, when in situ (e.g., at the articular region of a healthy or dysfunctioning joint).

In some particular embodiments, the liposome comprises a PC. In further particular embodiments, the liposome comprises a combination of two different PCs. In other particular embodiments, the liposome comprises a combination of a PC and SM.

In some embodiments, the liposomes are characterized in that they comprise at least one membrane comprising at least one phospholipid (PL) selected from a glycerophospholipid (GPL) having two, being the same or different, $C_{12}$-$C_{18}$ hydrocarbon chains and a sphingolipid (SPL) having a $C_{12}$-$C_{18}$ hydrocarbon chain. The phase transition temperature in which solid ordered (SO) to liquid disordered (LD) phase transition occurs, is within a temperature range of about 20° C. to about 39° C. The liposomes are used to lubricate joints that have a joint temperature that is higher than the phase transition temperature. Accordingly, the liposomes are in an LD phase within the joint.

It is noted that the above conditions are cumulative, namely, the selection of PL (either a single PL or a combination of PL with additional PLs) contained in the liposome is so that the liposome will have SO-LD phase transition temperature between about 20° C. to about 39° C.

The GPL or SPL can have alkyl, alkenyl or acyl $C_{12}$ to $C_{18}$ hydrocarbon chain. In the case of GPL, the two chains may be the same or different. In some embodiments, the GLP has $C_{12}$-$C_{16}$ hydrocarbon chains. In additional embodiments, the SPL has $C_{12}$-$C_{16}$ hydrocarbon chains.

One particular embodiment concerns the pharmaceutical composition comprising liposomes having GPL or SPL with at least one $C_{14}$ acyl chain. Another particular embodiment concerns the pharmaceutical composition comprising liposomes having GPL or SPL with at least one $C_{15}$ acyl chain. Yet another particular embodiment concerns the pharmaceutical composition comprising GPLs having at least one of $C_{14}$, $C_{15}$, $C_{16}$, and $C_{18}$ acyl chains. Still another particular embodiment concerns the pharmaceutical composition comprising liposomes having SPL with a $C_{16}$ acyl chain. Additional embodiments concern the pharmaceutical composition comprising a combination of any of the above liposomes.

In some embodiments at least one $C_{12}$-$C_{18}$ or $C_{12}$-$C_{16}$ hydrophobic chain is saturated. In further embodiments both $C_{12}$-$C_{18}$ and $C_{12}$-$C_{16}$ hydrophobic chains are saturated.

In one embodiment said $C_{12}$-$C_{18}$ or $C_{12}$-$C_{16}$ hydrophobic chains are unsaturated.

Non-limiting examples of the phospholipids which may be present in the liposome in accordance with the principles of the invention include 1,2-dimyristoyl-sn-glycero-3-phosphocholine (DMPC, $T_m$~24° C.); 1,2-dipalmitoyl-sn-glycero-3-phosphocholine (DPPC, Tm 41.4° C.); 1,2-dipentadecanoyl-sn-glycero-3-phosphocholine (C15, $T_m$ 33.0° C.); 1,2-distearoyl-sn-glycero-3-phosphocholine (DSPC), $T_m$ 55° C.); and N-palmitoyl-D-erythro-sphingosylphosphorylcholine (D-erythro C16, $T_m$ 41.0° C.). $T_m$ values of various PC-based lipids may be found in "Thermotropic Phase Transitions of Pure Lipids in Model Membranes and Their Modifications by Membrane Proteins", John R. Silvius, Lipid-Protein Interactions, John Wiley & Sons, Inc., New York, 1982, and also in the Lipid Thermotropic Phase Transition Data Base—LIPIDAT, and in Marsh (1990).

According to some embodiments, when using a mixture of two or more PLs, the mole ratio there between is designed such that the $T_m$ of the combination provides a liposome in LD phase when the pharmaceutical composition is administered to the joint. In further embodiments, the mole ratio is chosen to provide a liposome having a phase transition temperature in the range of about 20° C. to about 39° C.

In some embodiments, the liposome comprises DMPC. In further embodiments, the liposome consists essentially of DMPC. In still further embodiments, the at least one membrane of the liposome consists essentially of DMPC. In additional embodiments, the liposome consisting essentially of DMPC includes a tonicity agent having a concentration inside the liposome which is essentially the same as the concentration of the tonicity agent in the medium outside the liposome. In further embodiments, the liposome consisting essentially of DMPC includes a polyol having a concentration inside the liposome which is essentially the same as the concentration of the polyol in the medium outside the liposome. In still further embodiments, the liposome consisting essentially of DMPC includes mannitol having a concentration inside the liposome which is essentially the same as the concentration of mannitol in the medium outside the liposome.

In some embodiments, the pharmaceutical composition comprises a liposome comprising a combination of DMPC and an additional PC. In some embodiments, the pharmaceutical composition comprises a liposome comprising a combination of DMPC and an SPM.

In some embodiments, the mole percent of DMPC in the liposome membrane ranges from about 5% to about 100%. In further embodiments, the mole percent of DMPC in the liposome membrane ranges from about 5% to about 80%. In further embodiments, the mole percent of DMPC in the liposome membrane ranges from about 10% to about 75%, from about 15% to about 70%, from about 20% to about 65%, from about 25% to about 60%, from about 30% to about 55%, from about 35% to about 50%, from about 5% to about 15%, from about 20% to about 30%, from about 5% to about 30%, from about 40% to about 50%, or from about 70% to about 80%. Each possibility represents a separate embodiment of the invention. In some exemplary embodiments, the mole percent of DMPC in the liposome membrane is about 10%. In other exemplary embodiments, the mole percent of DMPC in the liposome membrane is about 25%. In further exemplary embodiments, the mole percent of DMPC in the liposome membrane is about 45%. In additional exemplary embodiments, the mole percent of DMPC in the liposome membrane is about 75%

In some embodiments, the liposome comprises a combination of DMPC and DPPC. In further embodiments, the liposome consists essentially of DMPC and DPPC. In still further embodiments, the at least one membrane of the liposome consists essentially of DMPC and DPPC. In additional embodiments, the liposome consisting essentially of DMPC and DPPC includes a tonicity agent having a concentration inside the liposome which is essentially the same as the concentration of the tonicity agent in the medium outside the liposome. In further embodiments, the liposome consisting essentially of DMPC and DPPC includes a polyol having a concentration inside the liposome which is essentially the same as the concentration of the polyol in the medium outside the liposome. In still further embodiments, the liposome consisting essentially of DMPC and DPPC includes mannitol having a concentration inside the liposome which is essentially the same as the concentration of mannitol in the medium outside the liposome.

In some embodiments, the mole percent ratio of DMPC to DPPC is in the range of about 25:75 to about 70:30. In further embodiments, the mole percent ratio of DMPC to DPPC is in the range of about 30:70 to about 65:25, from about 35:65 to about 60:30, or from about 40:60 to about 55:45. Each possibility represents a separate embodiment of the invention. In certain embodiments, the mole percent ratio of DMPC to DPPC is about 45:55. In additional embodiments, the mole percent ratio of DMPC to DPPC is about 25:75.

In some embodiments, the phase transition temperature of the liposome comprising a combination of DMPC and DPPC ranges between about 33° C. to about 37° C.

In some embodiments, the liposome comprises a combination of DMPC and C15. In further embodiments, the liposome consists essentially of DMPC and C15. In still further embodiments, the at least one membrane of the liposome consists essentially of DMPC and C15. In additional embodiments, the liposome consisting essentially of DMPC and C15 includes a tonicity agent having a concentration inside the liposome which is essentially the same as the concentration of the tonicity agent in the medium outside the liposome. In further embodiments, the liposome consisting essentially of DMPC and C15 includes a polyol having a concentration inside the liposome which is essentially the same as the concentration of the polyol in the medium outside the liposome. In still further embodiments, the liposome consisting essentially of DMPC and C15 includes mannitol having a concentration inside the liposome which is essentially the same as the concentration of mannitol in the medium outside the liposome.

In some embodiments, the mole percent ratio of DMPC to C15 is in the range of about 15:85 to about 55:45. In further embodiments, the mole percent ratio of DMPC to C15 is in the range of about 25:75 to about 45:55. In certain embodiments, the mole percent ratio of DMPC to C15 is about 45:55. In additional embodiments, the mole percent ratio of DMPC to C15 is about 25:75.

In some embodiments, the phase transition temperature of the liposome comprising a combination of DMPC and C15 ranges between about 29° C. to about 31° C.

In some embodiments, the at least one membrane comprises DMPC and DSPC. In further embodiments, the liposome consists essentially of DMPC and DSPC. In still further embodiments, the at least one membrane of the liposome consists essentially of DMPC and DSPC. In additional embodiments, the liposome consisting essentially of DMPC and DSPC includes a tonicity agent having a concentration inside the liposome which is essentially the same as the concentration of the tonicity agent in the medium outside the liposome. In further embodiments, the liposome consisting essentially of DMPC and DSPC includes a polyol having a concentration inside the liposome which is essentially the same as the concentration of the polyol in the medium outside the liposome. In still further embodiments, the liposome consisting essentially of DMPC and DSPC includes mannitol having a concentration inside the liposome which is essentially the same as the concentration of mannitol in the medium outside the liposome.

In some embodiments, the mole percent ratio of DMPC to DSPC is about 75:25.

In some embodiments, the phase transition temperature of the liposome comprising a combination of DMPC and DSPC is about 27° C.

In some embodiments, the liposome comprises a combination of DMPC and D-erythro C16. In further embodiments, the liposome consists essentially of DMPC and D-erythro C16. In still further embodiments, the at least one membrane of the liposome consists essentially of DMPC and D-erythro C16. In additional embodiments, the liposome consisting essentially of DMPC and D-erythro C16 includes a tonicity agent having a concentration inside the liposome which is essentially the same as the concentration of the tonicity agent in the medium outside the liposome. In further embodiments, the liposome consisting essentially of DMPC and D-erythro C16 includes a polyol having a concentration inside the liposome which is essentially the same as the concentration of the polyol in the medium outside the liposome. In still further embodiments, the liposome consisting essentially of DMPC and D-erythro C16 includes mannitol having a concentration inside the liposome which is essentially the same as the concentration of mannitol in the medium outside the liposome.

In some embodiments, the mole percent ratio of DMPC to D-erythro C16 is in the range of about 5:95 to about 50:50. In further embodiments, the mole percent ratio of DMPC to D-erythro C16 is in the range of about 10:90 to about 45:55, from about 10:90 to about 40:60, from about 10:90 to about 35:65, from about 10:90 to about 30:70, or from about 10:90 to about 25:75. Each possibility represents a separate embodiment of the invention. In some embodiments, the mole percent ratio of DMPC to D-erythro C16 is in the range of about 5:95 to about 50:50. In some exemplary embodiments, the mole percent ratio of DMPC to D-erythro C16 is about 10:90. In other exemplary embodiments, the mole percent ratio of DMPC to D-erythro C16 is about 25:75.

In some embodiments, the phase transition temperature of the liposome comprising a combination of DMPC and D-erythro C16 ranges between about 27° C. and 32° C.

In some embodiments, the liposome comprises C15. In further embodiments, the liposome consists essentially of C15. In still further embodiments, the at least one membrane of the liposome consists essentially of C15. In additional embodiments, the liposome consisting essentially of C15 includes a tonicity agent having a concentration inside the liposome which is essentially the same as the concentration of the tonicity agent in the medium outside the liposome. In further embodiments, the liposome consisting essentially of C15 includes a polyol having a concentration inside the liposome which is essentially the same as the concentration of the polyol in the medium outside the liposome. In still further embodiments, the liposome consisting essentially of C15 includes mannitol having a concentration inside the liposome which is essentially the same as the concentration of mannitol in the medium outside the liposome.

The total PL concentration in the pharmaceutical composition according to some embodiments of the invention ranges from about 20 mM to about 500 mM. In further embodiments, the concentration ranges from about 50 mM to about 300 mM. In still further embodiments, the concentration ranges from about 100 mM to about 200 mM. In yet further embodiments, the concentration ranges from about 130 mM to about 170 mM. In certain embodiments, the total PL concentration is about 150 mM.

In some embodiments, the total PL concentration ranges from about 10 mg/ml to about 500 mg/ml. In further embodiments, the concentration ranges from about 30 mg/ml to about 300 mg/ml. In still further embodiments, the concentration ranges from about 50 mg/ml to about 200 mg/ml. In certain embodiments, the total PL concentration is about 100 mg/ml.

In some embodiments, the phospholipids forming the liposomes are present in the pharmaceutical composition in a weight percent ranging from about 0.1% (w/w) to about 40% (w/w), from about 0.5% (w/w) to about 30% (w/w), from about 3% (w/w) to about 30% (w/w), or from about 1% (w/w) to about 20% (w/w) of the total weight of the pharmaceutical composition. In certain embodiments, the phospholipids forming the liposomes are present in the pharmaceutical composition in a weight percent of about 10% (w/w).

According to some embodiments, the liposomes suitable for use in the pharmaceutical composition of the present invention do not include in their bilayers a membrane active sterol, such as cholesterol. It is to be noted that the pharmaceutical composition of the present invention preferably does not contain propylene glycol. It should further be noted that the pharmaceutical composition of the present invention preferably does not contain dextran.

Additionally, it should be emphasized that the liposomes used in the pharmaceutical composition of the present invention are themselves used as an active ingredient and not as a carrier of a certain pharmaceutically active agent. As such and as mentioned hereinabove, the pharmaceutical compositions according to the principles of the present invention are essentially free of an additional pharmaceutically active agent. The term "essentially free of an additional pharmaceutically active agent", as used herein, refers in some embodiments to the pharmaceutical composition including less than a therapeutically effective amount of the pharmaceutically active agent, which is known for use in joint lubrication, treatment of joint dysfunction, reduction of joint pain, irritation and/or wear, or any combination thereof. The term "known for use", as used herein, refers in some embodiments, to pharmaceutically active agents approved for the indicated use at the time of the invention. In further embodiments, the term "known for use" refers to pharmaceutically active agents which will be approved for the indicated use in the future. In still further embodiments, the term "known for use" refers to pharmaceutically active agents which are mentioned in scientific literature and/or patents as being suitable for the indicated use.

In some embodiments, the pharmaceutical composition of the present invention does not include a pharmaceutically active agent which is a lubrication agent, such as, inter alia, glycosaminoglycan or a pharmaceutically acceptable salt, ester or derivative thereof. In certain embodiments, said glycosaminoglycan is hyaluronic acid or hyaluronan-containing salt or ester. In certain embodiments, hyaluronic acid is not encapsulated within the liposome. Additionally or alternatively, the hyaluronic acid should not be dispersed in the fluid medium. In some currently preferred embodiments, the pharmaceutical composition is being essentially free of hyaluronic acid, or a pharmaceutically acceptable salt or ester thereof. The term "essentially free", as used in connection with hyaluronic acid, refers in some embodiments to the pharmaceutical composition including less than a therapeutically effective amount of hyaluronic acid or its salt or ester. In additional embodiments, the term "essentially free" refers to the pharmaceutical composition including less than a detectable amount of hyaluronic acid or its salt or ester.

In some embodiments, the pharmaceutical composition of the present invention does not include a pharmaceutically active agent which is a lubrication agent selected from superficial zone protein (SZP), lubricin, proteoglycan 4 and analogs and derivatives thereof.

In some embodiments, the pharmaceutical composition of the present invention does not include a pharmaceutically active agent which is an anti-inflammatory agent, such as xylitol, betamethasone, prednisolone, piroxicam, aspirin, flurbiprofen, (+)-N-{4-[3-(4-fluorophenoxy)phenoxy]-2-cyclopenten-1-yl}-N-hydroxyurea salsalate, diflunisal, ibuprofen, fenoprofen, fenamate, ketoprofen, nabumetone, naproxen, diclofenac, indomethacin, sulindac, tolmetin, etodolac, ketorolac, oxaprozin, celecoxib, meclofenamate, mefenamic acid, oxyphenbutazone, phenylbutazone, salicylates, or phytosphingosine type agents.

In some embodiments, the pharmaceutical composition of the present invention does not include a pharmaceutically active agent which is an antiviral agent, such as acyclovir, nelfinavir, or virazole.

In some embodiments, the pharmaceutical composition of the present invention does not include a pharmaceutically active agent which is an antibiotic, including antibiotics belonging to the family of penicillines, cephalosporins, aminoglycosidics, macrolides, carbapenem and penem, beta-lactam monocyclic, inhibitors of beta-lactamases, and tetracyclins, polipeptidic antibiotics, chloramphenicol and derivatives, poly-etheric ionophores, and quinolones. Non-limiting examples of such antibiotics include ampicillin, dapsone, chloramphenicol, neomycin, cefaclor, cefadroxil, cephalexin, cephradine, erythromycin, clindamycin, lincomycin, amoxicillin, ampicillin, bacampicillin, carbenicillin, dicloxacillin, cyclacillin, picloxacillin, hetacillin, methicillin, nafcillin, oxacillin, penicillin G, penicillin V, ticarcillin, rifampin, tetracycline, fusidic acid, lincomicyn, novobiocine, and spectinomycin.

In some embodiments, the pharmaceutical composition of the present invention does not include a pharmaceutically active agent which is an anti-infective agent, such as benzalkonium chloride or chlorhexidine.

In some embodiments, the pharmaceutical composition of the present invention does not include a pharmaceutically active agent which is a steroid. The term "steroid", as used herein, refers to naturally occurring steroids and their derivatives as well as synthetic or semi-synthetic steroid analogues having steroid-like activity. The steroid can be a glucocorticoid or corticosteroid. Examples of specific natural and synthetic steroids include, but are not limited to: aldosterone, beclomethasone, betamethasone, budesonide, cloprednol, cortisone, cortivazol, deoxycortone, desonide, desoximetasone, dexamethasone, difluorocortolone, fluclorolone, flumethasone, flunisolide, fluocinolone, fluocinonide, fluocortin butyl, fluorocortisone, fluorocortolone, fluorometholone, flurandrenolone, fluticasone, halcinonide, hydrocortisone, icomethasone, mepredni sone, methylprednisolone, paramethasone, prednisolone, prednisone, tixocortol or triamcinolone, and their respective pharmaceutically acceptable salts or derivatives.

According to some embodiments, the phospholipids are used in the pharmaceutical composition of the present invention as a sole active ingredient.

According to some embodiments, the pharmaceutical composition consists essentially of the non-ionic tonicity agent comprising a polyol and the liposomes, as described herein. In some embodiments, the term "consisting essentially of" refers to a composition whose only active ingredient is the indicated active ingredient (i.e., liposomes), however, other compounds may be included which are for stabilizing, preserving, or controlling osmolarity, viscosity and/or pH of the formulation, but are not involved directly in the therapeutic effect of the liposomes and/or phospholipids. In some embodiments, the term "consisting" refers to a composition, which contains the liposomes, the tonicity agent and a pharmaceutically acceptable vehicle or excipient.

The pharmaceutical compositions according to the various embodiments of the invention can be sterilized and if desired mixed with auxiliary agents, e.g., preservatives, stabilizers, wetting agents, synthetic emulsifiers, additional salts for influencing osmotic pressure, coloring, and/or aromatic substances and the like which do not deleteriously react with the liposomes.

The GPL, SPL or their combinations form liposomes, preferably liposomes with a mean diameter greater than about 0.3 µm, greater than about 0.5 µm, greater than about 0.8 µm, or greater than about 1 µm. The mean diameter of the liposomes can be less than about 10 µm, 8 µm, 7 µm, 6 µm or 5 µm. Each possibility represents a separate embodiment of the invention. According to some embodiments, the liposomes have a mean diameter in the range of between about 0.3 µm and 10 µm. According to further embodiments, the liposomes have a mean diameter in the range of between about 0.5 µm and 9 µm. According to still further embodiments, the liposomes have a mean diameter in the range of between about 1 µm and 8 µm. According to yet further embodiments, the liposomes have a mean diameter in the range of between about 3 µm and 5 µm.

The terms "mean diameter" and "mean particle size" are used herein interchangeably, referring, in some embodiments to the mean diameter of a liposome derived from particle size distribution based on a number distribution model. In some embodiments, said terms refer to the mean diameter of a liposome derived from particle size distribution based on a volume distribution model. In additional embodiments, said terms refer to the mean diameter of a liposome derived from particle size distribution based on a surface area distribution model. Particle size distribution can be determined, inter alia, by laser light diffraction and/or by Coulter Counter method.

The liposomes may be a single-membrane liposome or may be, according to some embodiments, multilamellar vesicles (MLV) liposomes. According to other embodiments the liposomes may also be large multivesicular vesicles (LMVV) or dehydrated rehydrated vesicles (DRV) liposomes.

In some currently preferred embodiments, the liposomes are multilamellar vesicles (MLV). In certain such embodiments, the liposomes have more than one membrane.

According to one embodiment, the MLV are defined by a mean diameter in the range of between 0.3 µm and 10 µm. According to another embodiment, the MLV are defined by a mean diameter in the range of between 0.5 µm and 9 µm. According to still further embodiments, the MLV are defined by a mean diameter in the range of between about 1 µm and 8 µm. According to yet further embodiments, the MLV are defined by a mean diameter in the range of between about 3 µm and 5 µm.

In certain embodiments, the pharmaceutical composition comprises a polyol and MLV liposomes, which membranes consist essentially of DMPC and DPPC. The polyol can be selected from mannitol and glycerol. In a further embodiment, the pharmaceutical composition comprises mannitol and MLV liposomes, which membranes consist essentially of DMPC and DPPC. In an additional embodiment, the concentration of mannitol ranges between about 1 to about 70 mg/ml. In yet another embodiment, the pharmaceutical composition has osmolality in the range from about 200 to about 600 mOsm. In still another embodiment, the weight ratio between the liposomes and mannitol ranges from about 6:1 to about 2:1.

In some embodiments, the pharmaceutical composition comprises mannitol and MLV liposomes which membranes consist essentially of DMPC and DPPC. In some embodiments, DMPC is present in the pharmaceutical composition in a weight percent ranging from about 20% (w/w) to about 40% (w/w) of the dry weight of the pharmaceutical composition. In a certain embodiment, DMPC is present in the pharmaceutical composition in a weight percent of about 30% (w/w). In some embodiments, DPPC is present in the pharmaceutical composition in a weight percent ranging from about 30% (w/w) to about 60% (w/w) of the dry weight of the pharmaceutical composition. In a certain embodiment, DPPC is present in the pharmaceutical composition in a weight percent of about 40% (w/w). In some embodiments, mannitol is present in the pharmaceutical composition in a weight percent ranging from about 20% (w/w) to about 40% (w/w) of the dry weight of the pharmaceutical composition. In a certain embodiment, mannitol is present in the pharmaceutical composition in a weight percent of about 30% (w/w).

In some embodiments, the pharmaceutical composition comprising mannitol and liposomes which membranes consist essentially of DMPC and DPPC, further comprises histidine buffer as a fluid medium. In further embodiments, DMPC is present in the pharmaceutical composition in a weight percent ranging from about 1% (w/w) to about 10% (w/w) of the total weight of the pharmaceutical composition. In a certain embodiment, DMPC is present in the pharmaceutical composition in a weight percent of about 4% (w/w). In some embodiments, DPPC is present in the pharmaceutical composition in a weight percent ranging from about 2% (w/w) to about 12% (w/w) of the total weight of the pharmaceutical composition. In a certain embodiment, DPPC is present in the pharmaceutical composition in a weight percent of about 5% (w/w). In some embodiments, mannitol is present in the pharmaceutical composition in a weight percent ranging from about 1% (w/w) to about 7% (w/w) of the total weight of the pharmaceutical composition. In a certain embodiment, mannitol is present in the pharmaceutical composition in a weight percent of about 4% (w/w).

The pharmaceutical composition according to various embodiments of the invention can be used for the preparation of a replacement of naturally-occurring cartilage PLs, namely as a joint lubricant and/or wear reducer.

It is noted that the temperature of joints in patients afflicted with reduced joint lubrication or with joint wear, such as osteoarthritis varies as the disease proceeds [Hollander, J. L.; Moore, R., Studies in osteoarthritis using Intra-Articular Temperature Response to Injection of Hydrocortisone. *Ann. Rheum. Dis.* 1956, 15, (4), 320-326]. In fact, this temperature change was used as a clinical tool for assessing osteoarthritis inflammation [Thomas, D.; Ansell, B. M.; Smith, D. S.; Isaacs, R. J., Knee Joint Temperature Measurement using a Differential Thermistor Thermometer. *Rheumatology* 1980, 19, (1), 8-13]. In hand joints of osteoarthritis patients temperature was shown to vary from ~28 to ~33° C. [Varju, G.; Pieper, C. F.; Renner, J. B.; Kraus, V. B., Assessment of hand osteoarthritis: correlation between thermographic and radiographic methods. *Rheumatology* 2004, 43, 915-919], while the temperature of healthy Temporomandibular joint (TMJ) varies from ~35 to 37° C. [Akerman, S.; Kopp, S., Intra-articular and skin surface temperature of human temporomandibular joint. *Scand. J. Dent. Res.* 1987, 95, (6), 493-498].

Thus, in accordance with the principles of the invention it is essential and in fact a prerequisite that the PLs or the mixture thereof be in a LD phase, in situ, at the joint region to be lubricated therewith. In some embodiments, the liposomes have an offset temperature (upper limit) of the SO to LD phase transition which is not higher than 15° C. from the temperature in situ, i.e. in the joint, within the range of about 20° C. to about 39° C. In accordance with the principles of the invention the liposomes are formed from GPL, SPL or their combination, and the SO to LD phase transition temperature described above thus concerns liposomes which are formed from GPL, SPL and combinations thereof, thus providing a liposome in which the PLs or their mixture are in LD phase.

In certain embodiments, the non-ionic tonicity agent comprising polyol does not affect the phase transition temperature of the liposomes. In further embodiments, the phase transition temperature of the liposomes combined with the non-ionic tonicity agent comprising polyol differs from the phase transition temperature of the liposomes alone by no more than about 10%. In still further embodiments, the phase transition temperature of the liposomes combined with the non-ionic tonicity agent comprising polyol differs from the phase transition temperature of the liposomes alone by no more than about 5%.

The pharmaceutical composition of the invention may be used to treat, alleviate, retard, prevent, manage or cure any articular disorder or symptoms arising therefrom which is associated with joint dysfunction. The term "articular disorder", as used herein, should be held to mean any affliction (congenital, autoimmune or otherwise), injury or disease of the articular region which causes degeneration, pain, reduction in mobility, inflammation, irritation, or physiological disruption and dysfunction of joints. The disorder may be associated with reduced joint secretion and lubrication as well as from complications of knee and hip replacement.

The joint in accordance with the principles of the invention may be any one of the knee, hip, ankle, shoulder, elbow, tarsal, carpal, interphalangeal and intervertebral. Each possibility represents a separate embodiment of the invention. In certain embodiments, said joint is a knee joint.

Specific articular disorders include, but are not limited to, deficiencies of joint secretion and/or lubrication arising from arthritis, including conditions of joint erosion in rheumatoid arthritis, osteoarthritis, osteoarthritis in rheumatoid arthritis patients, traumatic joint injury (including sports injury), locked joint (such as in temporomandibular joint (TMJ)), status post arthrocentesis, arthroscopic surgery, open joint surgery, joint (e.g. knee or hip replacement) in mammals, preferably humans. A preferred disorder to be treated or prevented by use of the pharmaceutical composition of the invention is osteoarthritis.

In certain embodiments, the pharmaceutical composition is for the reduction of knee joint pain in osteoarthritis patients.

The pharmaceutical composition of the present invention could be used as a prophylactic measure to prevent future damage or degeneration. For example, the pharmaceutical composition could be administered intra-articularly to athletes intermittently throughout their career to minimize the risk of stress related injury or cartilage degeneration.

The pharmaceutical composition of the present invention may be administered exclusive of, or as an adjunct to, anti-inflammatory agents, analgesic agents, muscle relaxants, anti-depressants, or agents that promote joint lubrication commonly used to treat disorders associated with joint stiffness, such as arthritis. A combined therapeutic approach is beneficial in reducing side effects associated with agents, such as non-steroidal, anti-inflammatory drugs (NSAIDs), commonly used to prevent, manage, or treat disorders such as osteoarthritis associated with reduced joint lubrication. In addition to enhancing safety, a combined therapeutic approach may also be advantageous in increasing efficacy of treatment.

In some embodiments, the pharmaceutical composition is in a form suitable for parenteral administration. The parenteral administration of the pharmaceutical composition of the invention into an articular cavity of a patient can be performed by a method chosen from the group consisting of intra-articular injection, arthroscopic administration or surgical administration. Accordingly, in some embodiments, the pharmaceutical composition is formulated in a form suitable for administration by a route selected from intra-articular injection, arthroscopic administration or by surgical administration. One of the beneficial features of the disclosed pharmaceutical composition is the presence of the tonicity agent, which adjusts the osmolality of the liposomal composition to a physiological value, thereby reducing the side effects associated with the intra-articular administration.

The pharmaceutical composition according to the various embodiments of the invention may be administered in a dose of from about 0.5 ml to about 10 ml. In further embodiments, the pharmaceutical composition is administered in a dose of from about 1 ml to about 6 ml. In certain embodiments, the pharmaceutical composition is administered in a dose of about 3 ml.

In some embodiments, one dosage unit of the pharmaceutical composition comprises from about 20 mg to about 350 mg mannitol. In some embodiments, one dosage unit of the pharmaceutical composition comprises from about 40 mg to about 250 mg mannitol. In a certain embodiment, one dosage unit of the pharmaceutical composition comprises about 120 mg mannitol. In another embodiment, one dosage unit of the pharmaceutical composition comprises about 40 mg mannitol. In additional embodiment, one dosage unit of the pharmaceutical composition comprises about 250 mg mannitol.

In some embodiments, one dosage unit of the pharmaceutical composition comprises from about 50 mg to about 1000 mg phospholipids. In some embodiments, one dosage unit of the pharmaceutical composition comprises from about 100 mg to about 800 mg phospholipids. In a certain embodiment, one dosage unit of the pharmaceutical composition comprises about 300 mg phospholipids. In another certain embodiment, one dosage unit of the pharmaceutical composition comprises about 100 mg phospholipids. In additional embodiment, one dosage unit of the pharmaceutical composition comprises about 600 mg phospholipids.

In some embodiments, one dosage unit of the pharmaceutical composition comprises from about 30 mg to about 550 mg DPPC. In some embodiments, one dosage unit of the pharmaceutical composition comprises from about 50 mg to about 500 mg DPPC. In a certain embodiment, one dosage unit of the pharmaceutical composition comprises about 180 mg DPPC. In another embodiment, one dosage unit of the pharmaceutical composition comprises about 60 mg DPPC. In additional embodiment, one dosage unit of the pharmaceutical composition comprises about 365 mg DPPC.

In some embodiments, one dosage unit of the pharmaceutical composition comprises from about 20 mg to about 450 mg DMPC. In some embodiments, one dosage unit of the pharmaceutical composition comprises from about 40 mg to about 300 mg DMPC. In a certain embodiment, one dosage unit of the pharmaceutical composition comprises about 140 mg DPPC. In another embodiment, one dosage unit of the pharmaceutical composition comprises about 45 mg DPPC. In a certain embodiment, one dosage unit of the pharmaceutical composition comprises about 275 mg DPPC.

The pharmaceutical composition can be portioned in vials or in single injections or any other convenient way for practical use.

Subjects to which administration of the pharmaceutical compositions of the invention is contemplated include mammals, such as, but not limited to, humans and other primates.

Throughout the description and claims of this specification, the singular forms "a" "an" and "the" include plural references unless the context clearly dictates otherwise. Thus, for example, a reference to "a PL" is a reference to one or more PLs and "a liposome" refers to one or more liposomes. Throughout the description and claims of this specification, the plural forms of words include singular references as well, unless the context clearly dictates otherwise. It should be noted that the term "and" or the term "or" is generally employed in its sense including "and/or" unless the content clearly dictates otherwise.

Yet, throughout the description and claims of this specification, the words "comprise" and "contain" and variations of the words, for example "comprising" and "comprises", mean "including but not limited to", and are not intended to (and do not) exclude other moieties, additives, components, integers or steps.

As used herein, the term "about", when referring to a measurable value such as an amount, a temporal duration, and the like, is meant to encompass variations of +/−10%, more preferably +/−5%, even more preferably +/−1%, and still more preferably +/−0.1% from the specified value, as such variations are appropriate to perform the disclosed methods.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Materials and Methods
Materials
1,2-Dimyristoyl-sn-Glycero-3-Phosphocholine (DMPC 14:0, Cat: 556200), 1,2-Dipalmitoyl-sn-Glycero-3-Phosphocholine (DPPC 16:0, Cat: 556300) were obtained from Lipoid (Ludwigshafen, Germany). 1,2-Distearoyl-sn-Glycero-3-Phosphocholine (DSPC 18:0, Cat: 850365P), 1,2-dipentadecanoyl-sn-Glycero-3-Phosphocholine (C15 (also abbreviated herein as PC (15:0)), Cat: 850350P) were obtained from Avanti Polar Lipids (Alabaster, Ala., USA). N-Palmitoyl-D-erythro-Sphingosylphosphorylcholine (Palmitoyl Sphingomyelin, D-erythro C16 (also abbreviated herein as C16 SPM), Cat: 16608050) was obtained from Bio-Lab ltd. (Jerusalem, Israel)

Highly pure water (resistance of 18.2 megaOhm) was obtained using the WaterPro PS HPLC/Ultrafilter Hybrid System (Labconco, Kansas City, Mo.). HPLC-grade ethanol was obtained from BioLab Ltd, Jerusalem, Israel. L-histidine mono hydrochloride monohydrate, Sodium hydroxide (NaOH) and D-Mannitol were all obtained from Merck (Darmstadt, Germany). Glycerol was obtained from Merck, cat no. 1.04093. Sodium chloride was obtained from J. T. Baker, cat no. 4058-02

Methods
Preparation of Hypotonic Compositions Comprising MLV Liposomes
A mixture of the desired phospholipids was dissolved in 2.5 ml ethanol to a concentration of 180 mM. This solution was stirred by vortex and placed in water bath (60° C.) for ~20 minutes. Stirring was repeated for several times until the phospholipids were fully dissolved. The ethanolic solution was transferred into 10 ml warm 10 mM or 7.5 mM histidine buffer (pH 6.5) mixed vigorously by vortex for 2 min in order to hydrate the lipids and form a dispersion of the desired MLV.

Ethanol was removed by 5 cycles of centrifugation and cold buffer replacement at 4° C. For liposomal systems consisting of PCs centrifuge was done at 3000 rpm, for 40 minutes in the 1st cycle and 30 minutes at 4000 rpm in subsequent cycles. For liposomal systems comprising SPL centrifuge was done at 4000 rpm, for 50 minutes twice with an overnight standby in-between in the 1st cycle, and twice for 40 minutes at 4000 rpm in cycles 2 and 3. Cycles 4 and 5 were done for 60 min at 4000 rpm. Monitoring on ethanol removal was done by osmolality measurements. After every cold buffer replacement, the pellets were resuspended using a sterile pipette to loosen the sticky pellet, then the tubes are closed tightly and vortexed for 2 minutes. The centrifugation process and solution replacement were repeated until the osmolality in the mixture was less than 50 mOsm. The osmotic pressure of HB (10 mM, 7.5 mM) was measured and was found to be 26 and 19 mOsm, respectively. MLV were stored at 2-8° C. until analysis.

Preparation of Isotonic Compositions Comprising MLV Liposomes and a Tonicity Agent The liposomes were prepared as described hereinabove. The ethanolic solution of the liposomes was transferred into 10 ml warm 13.5 mM histidine buffer (pH 6.5) comprising a tonicity agent selected from mannitol, glycerol and sodium chloride and mixed vigorously by vortex for 2 min in order to hydrate the lipids and form a dispersion of the desired MLV.

Concentrations of the tonicity agents in the histidine buffer were as follows: Glycerol—235 mM; Mannitol—234 mM; and NaCl—131 mM.

The centrifugation process and solution replacement were repeated until the osmolality in the mixture was about 300 mOsm. The compositions were stored at 2-8° C. until analysis.

MLV Liposomes Characterization
Phospholipid concentration was determined using a modified Bartlett method [Barenholz, Y. and S. Amselem, *Quality control assays in the development and clinical use of liposome-based formulations*. Liposome technology, 1993. 1: p. 527-616]. Liposome size distribution was determined by laser diffraction particle size analyzer (LS13320 Beckman Coulter), which enables measuring particle size in the range of 40 nm to 2 mm. Coulter Counter method (which is based on measuring the changes in electrical conductance as particles suspended in a conductive fluid pass through a small orifice) was also used for size distribution determination.

The Cartilage-On-Cartilage Ex Vivo Model for the Lubrication Efficiency Evaluation Normal articular cartilage from donors (Ages: male 70 yrs and female 68, 72, 81, 87, 98 yrs.) were obtained from operations of femoral head fractures at the Hadassah Medical Center, Jerusalem. Tissue was frozen at −20° C. until analyzed.

Synovial fluid was pooled from 8 donors at the Hadassah Medical Center, Jerusalem.

Reagents used for the preparation of cartilage specimens included Superglue (cyanoacrylate adhesive, 3 g), NaCl (Bio Lab LTD, Israel, 19030291 Cat no: 19030291 Lot. no: 57747), and ethanol (Frutarom, Israel, Cat no: 5551640 Lot. no: 26141007).

Samples were prepared in the laboratory of Cartilage and Joints Diseases, the Department of Biomedical Engineering Technion, ITT, Haifa, Israel. Tests were performed at the Shamban & Microsystems Tribology Laboratories, the Department of Mechanical Engineering Technion, ITT, Haifa, Israel. The in-house apparatus for friction measurements was equipped with load cell with a strain gauge measuring system (HBM Z8, Germany) and LabView software (National Instruments, USA).

The apparatus was set up as follows. The cartilage plugs were prepared and fixed. From every cartilage, 10-20 plugs, of either 4 mm or 8 mm in diameter were prepared. These plugs were randomly assigned to the various tested formulations. The 8 mm plugs were mounted in the apparatus on the fixed holder and submerged in a solution containing 2 ml of synovial fluid (SF) and the tested solution in a 1:1 ratio (v/v). The 4 mm plugs were fixed on the upper piston.

Measurements: The friction test was performed with multiple repetitions in the presence of the different tested samples. For every measurement, the upper plug was positioned over the bottom plug, and following several seconds dwelling interval, the friction coefficient was measured. For any given pair of plugs, not less than 10 independent measurements were performed, with the plugs being rotated before each subsequent test for providing similar conditions in all repetitions.

Static friction coefficient was determined under specific tribological conditions of applied load, sliding velocity, dwell time and temperature, as shown in Table 1:

TABLE 1

| Cartilage-on-cartilage model experimental conditions: | |
| --- | --- |
| Normal load | 30 N |
| Sliding velocity | 1 mm s$^{-1}$ |
| Dwell time (duration of loading before sliding start) | 5 s |
| Sliding distance | 5 mm |
| Lubricant temperature | 32 to 34° C. |

Differential Scanning Calorimetric (DSC) Measurements

For determination of the $T_m$ of the different liposomal systems, samples were scanned using MicroCal™ VP-DSC GE Healthcare Life Sciences (Uppsala, Sweden, now owned by Malvern UK). Samples of MLV in HB and of a pharmaceutical composition comprising liposomes and mannitol, at a concentration of about 20 mM phospholipid, with HB or HB with mannitol in the reference cell, were scanned in the range between 10° and 75° C., at the heating rate of 1° C./min. Each sample studied was scanned three times at the same rate—increasing the temperature from 10° C. to 75° C. (scan 1), decreasing the temperature from 75° C. to 10° C. (scan 2) and again increasing the temperature from 10° C. to 75° C. (scan 3). Processing of the calorimetric data was done by the Origin® 7.0 software. $T_{on}$ and $T_{off}$ of the main phase transition were determined by extrapolating a straight line to define the temperature range of the main phase transition. For system F1 additional analysis by fitting Model: MN2State was done due to a broad "shoulder" in peak 2.

Example 1

Effect of the Tonicity Agent on the Lubrication Properties of the Liposomal Pharmaceutical Composition Cartilage lubrication by the pharmaceutical composition comprising a tonicity agent and liposome was evaluated using cartilage-on-cartilage ex vivo model. The cartilage-on-cartilage ex vivo model offers an experimental system to test the relative effect of bio-lubricant preparations on the static friction coefficient. This type of measurement may be indicative of the ability of different lubricants to reduce cartilage friction coefficient. The cartilage-on-cartilage ex vivo model utilizes an apparatus where two fixed human cartilage plugs are allowed to slide one over the other while submerged in different lubricants solutions. The apparatus enables measurement of static friction between the two cartilage specimens [Merkher Y et al. "A rational human joint friction test using a human cartilage-on-cartilage." Tribology Letters (2006): 29-36]. This model has been used in the past in order to compare the friction coefficient of different liposomal compositions [Sivan S et al. "Liposomes act as effective biolubricants for friction reduction in human synovial joints." Langmuir (2010): 1107-16].

The present experiment was designed to determine the relative lubrication properties of liposomal formulations comprising a tonicity agent, as reflected by the static friction coefficient measurements and to compare them to the hypotonic liposomal formulation. Table 2 presents the pharmaceutical compositions, which were tested. The chosen liposomal combination was DMPC/DPPC with a mole percent ratio of 45:55.

TABLE 2

| Hypotonic and isotonic liposomal compositions | | | |
| --- | --- | --- | --- |
| Formulation # | Phospholipid (mole percent ratio) | Tonicity agent | Fluid medium |
| 1 | DMPC/DPPC (45:55) | — | Histidine Buffer |
| 2 | DMPC/DPPC (45:55) | Glycerol | Histidine Buffer |
| 3 | DMPC/DPPC (45:55) | Mannitol | Histidine Buffer |
| 4 | DMPC/DPPC (45:55) | NaCl | Histidine Buffer |

The liposomal compositions comprised 183 mg of DPPC and 136 mg of DMPC dispersed in 3 ml of 10 mM Histidine buffer (HB) pH 6.5. The liposomal compositions comprising the 10 mM Histidine buffer had an osmolarity of about 50 mOsm (Table 3). Accordingly, in order to increase the osmolarity to the isotonic level of about 300 mOsm, the concentration of the tonicity agent should be adjusted to provide about 250 mM solute.

Mannitol was added in the amount of 120 mg (4% wt. or 40 mg/ml) to form an isotonic composition. Glycerol was added in the amount of 61 mg (2% wt. or 20 mg/ml). Sodium chloride was added in the amount of 21 mg.

Table 3 summarizes the physicochemical properties of the different liposomal compositions. Liposomal compositions were prepared with three different tonicity agents, each has equal contribution to the overall osmolality of the preparation. The isotonicity of these preparations was about 300 mOsm. A comparison between ionic (NaCl) and non-ionic (mannitol and glycerol) tonicity agents was performed. A hypotonic liposomal composition without a tonicity agent (less than 50 mOsm) was also tested. The effect of the tonicity agent on the lubrication ability of the liposomal composition was assessed using the cartilage-on-cartilage model setup, as described in Materials and Methods.

TABLE 3

| Physicochemical properties of the liposomal compositions. | | | | |
| --- | --- | --- | --- | --- |
| | | Isotonic formulations | | |
| | Buffer | Mannitol | Glycerol | NaCl |
| pH | 6.6 | 6.4 | 6.4 | 6.4 |
| Osmolality (mOsm) | 49 | 307 | 299 | 289 |
| Particle size by volume (μm) | 5.8 | 4.4 | 3.8 | 4.5 |

TABLE 3-continued

Physicochemical properties of the liposomal compositions.

| | Isotonic formulations | | | |
|---|---|---|---|---|
| | Buffer | Mannitol | Glycerol | NaCl |
| Particle size by surface area (μm) | 3.4 | 2.8 | 2.9 | 3.2 |
| Particle size by number (μm) | 1.3 | 1.5 | 1.7 | 1.8 |
| Assay DMPC (mM) | 66.4 | 67.5 | 70.2 | 69.6 |
| Assay DPPC (mM) | 81.7 | 82.1 | 84.7 | 83.3 |
| Phospholipid concentration (mM) | 148 | 150 | 155 | 153 |
| Mole percent ratio DMPC/DPPC | 55.2/44.8 | 45.1/54.9 | 45.3/54.7 | 45.5/54.5 |
| Lyso-myristoyl phosphatidylcholine (%) | NMT* 0.5 | ND** | ND | ND |
| Lyso-palmitoyl phosphatidylcholine (%) | NMT 0.5 | ND | ND | ND |
| Mystic acid (%) | 0.27 | ND | ND | ND |
| Palmitic Acid (%) | 0.27 | 0.06 | 0.04 | ND |
| Total impurities | LT*** 0.2 | 0.06 | 0.04 | ND |

*NMT - Not more than
**ND - Not detected
***LT - Less than

Table 4 presents preliminary results of average static friction coefficients obtained in the experiment. The precision of measurements repetitions is similar among all tested formulations, as reflected by the relative SD.

TABLE 4

Lubrication properties of the liposomal compositions.

| Formulation | Buffer | Glycerol | Mannitol | NaCl |
|---|---|---|---|---|
| Number of repetitions | 53 | 55 | 56 | 50 |
| Av. Static Friction Coefficient | 0.093 | 0.075 | 0.064 | 0.098 |
| S.D. | 0.025 | 0.020 | 0.022 | 0.026 |

Comparison of formulations revealed that the preparation containing mannitol exhibited the lowest static friction coefficient as compared with other isotonic formulations. The lowest static friction coefficient indicates that the mannitol formulation possesses higher lubrication properties. It was surprisingly found that the static friction coefficient obtained when using the mannitol formulation was about 30% lower than when using the hypotonic liposomal composition without a tonicity agent. The glycerol formulation also provided better lubrication (about 20% lower average static friction coefficient as compared to the hypotonic formulation). In contrast, addition of the ionic tonicity to the liposomal composition agent did not enhance lubrication ability thereof.

Example 2

Effect of the Tonicity Agent on the Thermotropic Properties of the Liposomal Pharmaceutical Compositions The present experiment was designed to determine whether the addition of a tonicity agent affects the thermotropic behavior and thermodynamic parameters of the liposomal composition, including the range of the SO-LD phase transition ($T_{on} \rightarrow T_{off}$), $T_p$, $T_m$, $T_{1/2}$, and $\Delta H$. $T_{on}$ and $T_{off}$ represent the temperature at which the SO-LD phase transition was initiated and ended during heating scans, $T_p$, and $T_m$ represent the temperature at which the maximum change in the heat capacity during the pre-transition ($T_p$) and main transition ($T_m$) occurs, $T_{1/2}$ represent the temperature (width) range at half height of the endotherm representing the change of enthalpy during the SO-LD phase transition and $\Delta H$ is the area under the curve representing the total change in enthalpy during the SO-LD phase transition.

Two types of liposomal compositions were chosen, each one was tested with and without mannitol (as a tonicity agent). The tested liposomal compositions are presented in Table 5.

TABLE 5

Hypotonic and isotonic liposomal compositions

| Phospholipid (mole percent ratio (where applicable) | Tonicity agent | Fluid medium |
|---|---|---|
| DMPC/DPPC (45:55) | — | Histidine Buffer |
| DMPC/DPPC (45:55) | Mannitol | Histidine Buffer |
| 1,2-dipentadecanoyl-sn-glycero-3-phosphocholine (C15) | — | Histidine Buffer |
| 1,2-dipentadecanoyl-sn-glycero-3-phosphocholine (C15) | Mannitol | Histidine Buffer |

The DMPC/DPPC liposomal compositions comprised 183 mg of DPPC and 136 mg of DMPC dispersed in 3 ml of 10 mM Histidine buffer (HB) pH 6.5. The C15 liposomal composition comprised 212 mg (70.6 mg/ml) phospholipid. Mannitol was added in the amount of 120 mg (4% wt.) to form isotonic compositions.

Table 6 summarizes the physicochemical properties of the different liposomal compositions.

TABLE 6

Physicochemical properties of the liposomal compositions.

| Phospholipid | Tonicity agent | Total PCs (mM) | MLV osmolality (mOsm) | Size distribution by volume | | |
|---|---|---|---|---|---|---|
| | | | | Av. Mean (μm) | Median (μm) | S.D. |
| DMPC/DPPC | — | 105 | 34 | 2.7 | 2.18 | 1.73 |
| DMPC/DPPC | mannitol | 91 | 288 | 4.24 | 2.70 | 4.61 |
| C15 | — | 102.7 | 28 | 3.97 | 2.59 | 3.96 |
| C15 | mannitol | 99.3 | 272 | 3.1 | 2.61 | 1.96 |

For determination of the thermotropic behavior and thermodynamic parameters ($T_{on} \rightarrow T_{off}$, $T_m$, $T_{1/2}$, $\Delta H$) of the different systems, samples were scanned using MicroCal™ VP-DSC (GE Healthcare Life Sciences, Uppsala, Sweden). Processing of the calorimetric data was done by the Origin® 7.0 software. The way $T_{on} \rightarrow T_{off}$ range was determined is described in Materials and Methods.

Table 7 presents thermotropic characterization of the tested liposomal compositions assessed from the DSC scans

TABLE 7

Thermotropic characterization of the liposomal compositions.

| | | Peak 1 (pre-transition) | | | | | Peak 2 (phase-transition) | | | | |
|---|---|---|---|---|---|---|---|---|---|---|---|
| Phospholipid | Tonicity agent | $T_{on}$ (° C.) | $T_{off}$ (° C.) | $T_p$ (° C.) | $T_{1/2}$ (° C.) | ΔH (Cal/mole) | $T_{on}$ (° C.) | $T_{off}$ (° C.) | $T_m$ (° C.) | $T_{1/2}$ (° C.) | ΔH (Cal/mole) |
| DMPC/DPPC | — | 17.8 | 24.7 | 21.0 | 2.2 | 1030.5 | 30.44 | 35.19 | 33.6 | 3.5 | 9782.1 |
| DMPC/DPPC | mannitol | 17.6 | 24.5 | 21.0 | 2.5 | 962.7 | 30.49 | 35.42 | 33.7 | 3.3 | 10707.7 |
| C15 | — | 21.7 | 27.3 | 24.6 | 2.2 | 1316.9 | 33.03 | 35.16 | 34.3 | 1.3 | 6716.9 |
| C15 | mannitol | 20.5 | 27.0 | 24.5 | 2.5 | 1009.1 | 32.66 | 35.29 | 34.4 | 1.5 | 6081.3 |

Figure 2:
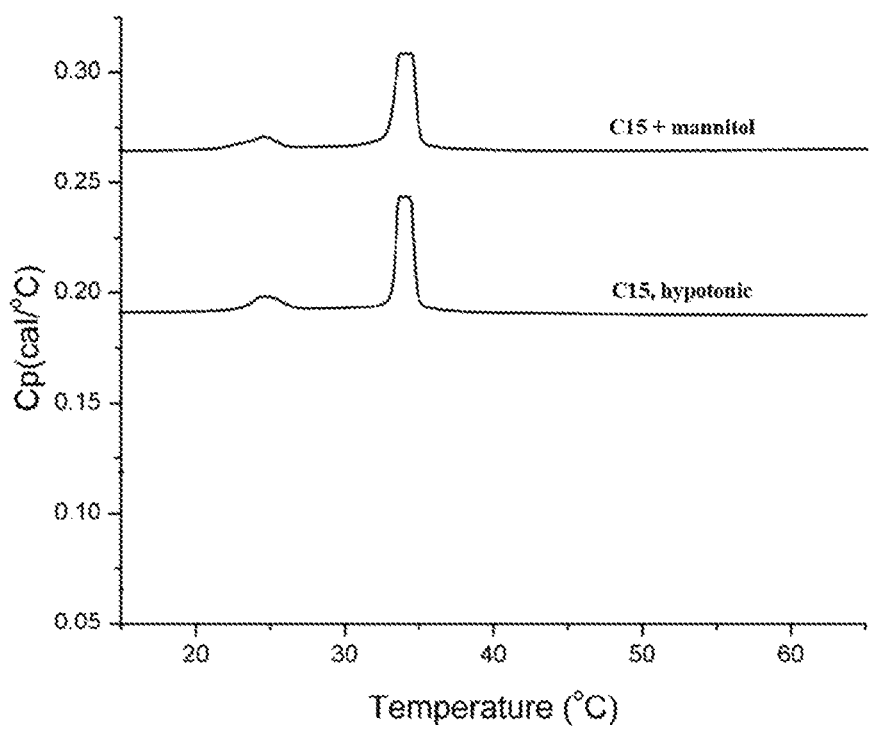
FIG. 2 shows raw Differential Scanning calorimetry (DSC) thermograms of isotonic and hypotonic liposomal compositions comprising C15.

The results summarized in Table 7 and FIGS. 1 and 2 indicate lack of mannitol effect on the thermotropic behavior of DMPC/DPPC 45/55 mole ratio MLV and of 100 mole % C15 MLV.

Example 3

Phase Transition Temperatures of the Liposomal Combinations

The present study was configured to assess the thermotropic behavior and thermodynamic parameters of various liposomal compositions and in particular to find liposomal combinations having phase transition temperatures in the range of 20° C. to 39° C. Since the addition of mannitol does not affect thermotropic behavior of the liposomes (as was shown in Example 2), the phase transition temperatures of the various liposomal compositions tested in the present study should be similar to the that of the corresponding isotonic compositions.

The tested liposomal compositions are presented in Table 8.

TABLE 8

Liposomal compositions

| | Phospholipid (mole %) | | | | | | |
|---|---|---|---|---|---|---|---|
| System | DMPC | DPPC | DSPC | C15 | D-erythro C16 | Buffer | Expected $T_m$ |
| A1 | 0 | 100 | — | — | — | HB | 41° C. |
| B1 | 10 | 90 | — | — | — | HB | <41° C. |
| C1 | 25 | 75 | — | — | — | HB | <<41° C. |
| D1 | 45 | 55 | — | — | — | HB | ~34° C. |
| F1 | 75 | — | 25 | — | — | HB | <<55° C. |
| G1 | 45 | — | — | 55 | — | HB | <<35° C. |
| H1 | 25 | — | — | 75 | — | HB | <35° C. |
| A2 | — | — | — | — | 100 | HB | ~41° C. |
| B2 | 10 | — | — | — | 90 | HB | <41° C. |
| C2 | 25 | — | — | — | 75 | HB | <41° C. |
| D2 | 75 | — | — | — | 25 | HB | <<41° C. |
| E2 | 90 | — | — | — | 10 | HB | <<41° C. |
| F2 | 100 | — | — | — | — | HB | ~24° C. |
| G2 | — | — | — | 100 | — | HB | ~34° C. |

The different MLV systems were characterized for size distribution, osmolality and total PC concentrations. The results are summarized in tables 9-12.

TABLE 9

Physicochemical properties of MLV of different DPPC: DMPC mixtures

| System PC ratio (mole %) | Total PCs (mM) | MLV osmolality (mOsm) | Size distribution by volume | | |
|---|---|---|---|---|---|
| | | | Av. Mean (μm) | Median (μm) | S.D. |
| A1 DPPC 100 | 93 | 31 | 3.12 | 2.4 | 2.38 |
| B1 DMPC/DPPC 10/90 | 111 | 29 | 3.10 | 2.34 | 2.31 |
| C1 DMPC/DPPC 25/75 | 107 | 27 | 3.92 | 2.64 | 4.03 |
| D1 DMPC/DPPC 45/55 | 105 | 34 | 2.7 | 2.18 | 1.73 |
| F2 DMPC 100 | 136.5 | 32 | 2.93 | 1.87 | 3.02 |

Based on osmolality results described in this table, the ethanol level is below 0.1% for all MLV systems. Based on the Liposome/water partition coefficient, most of it is in the aqueous phase.

TABLE 10

Physicochemical properties of MLV of DSPC: DMPC mixture

| System PC ratio (mole %) | Total PCs (mM) | MLVs osmolality (mOsm) | Size distribution by volume | | |
|---|---|---|---|---|---|
| | | | Av. Mean (μm) | Median (μm) | S.D |
| F1 DMPC/DSPC 75/25 | 69 | 50 | 3.72 | 3 | 2.77 |

Based on osmolality results described in this table the ethanol level is below 0.2%. Based on the Liposome/water partition coefficient, most of it is in the aqueous phase. This MLV represent a major lipid loss which occurred during the removal of the ethanol.

TABLE 11

Physicochemical properties of MLV of different C15:DMPC mixtures

| System PC ratio (mole %) | Total PCs (mM) | MLVs osmolality (mOsm) | Size distribution by volume | | |
|---|---|---|---|---|---|
| | | | Av. Mean (μm) | Median (μm) | S.D |
| G2 PC(15:0) 100 | 102.7 | 28 | 3.97 | 2.59 | 3.96 |
| G1 DMPC/PC15 45/55 | 103 | 40 | 4.57 | 3.44 | 3.84 |

TABLE 11-continued

Physicochemical properties of MLV of different C15:DMPC mixtures

| System PC ratio (mole %) | Total PCs (mM) | MLVs osmolality (mOsm) | Size distribution by volume | | |
|---|---|---|---|---|---|
| | | | Av. Mean (μm) | Median (μm) | S.D |
| H1 DMPC/PC15 25/75 | 97 | 34 | 3.06 | 2.16 | 2.38 |

Based on osmolality results described in this table, the ethanol level is below 0.1% for all MLV systems. Based on the Liposome/water partition coefficient, most of it is in the aqueous phase.

TABLE 12

Physicochemical properties of MLV of different DMPC/D-erythro C16 mixtures

| System PC ratio (mole %) | Total PCs (mM) | MLVs osmolality (mOsm) | Size distribution by volume | | |
|---|---|---|---|---|---|
| | | | Av. Mean (μm) | Median (μm) | S.D |
| A2 D-erythro C16 100 | 53.9 | 20 | 4.04 | 2.66 | 4.38 |
| B2 DMPC/D-erythro C16 10/90 | 76.6 | 20 | 3.31 | 2.27 | 3.25 |
| C2 DMPC/D-erythro C16 25/75 | 85.7 | 21 | 3.37 | 2.31 | 3.18 |
| D2 DMPC/C16 D-erythro C16 75/25 | 90.4 | 24 | 2.67 | 2.05 | 1.83 |
| E2 DMPC/D-erythro C16 10/90 | 56.6 | 22 | 3.7 | 3.03 | 2.5 |
| F2 DMPC 100 | 136.5 | 32 | 2.93 | 1.87 | 3.02 |

Based on osmolality results described in this table, the ethanol level is below 0.1% for all MLV systems. Based on the Liposome/water partition coefficient, most of it is in the aqueous phase.

Figure 3:
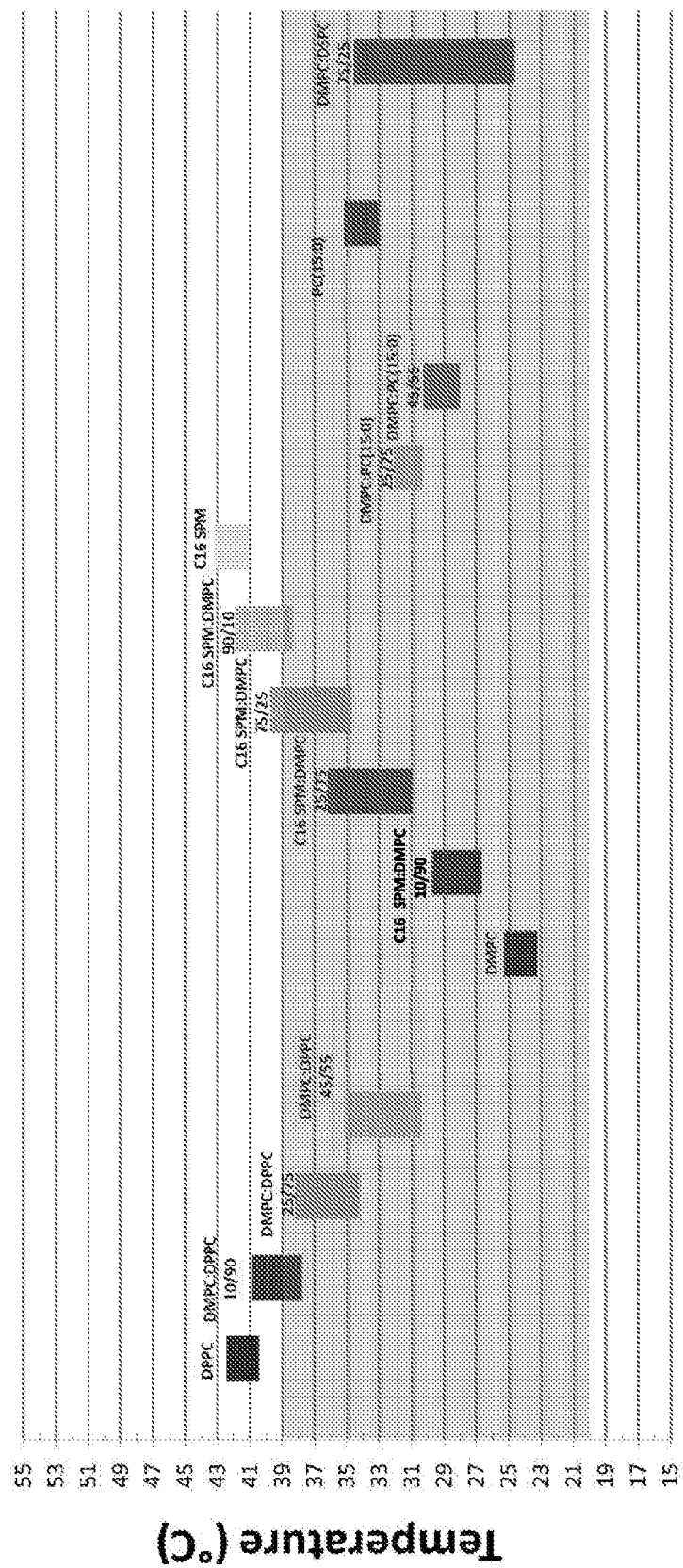
FIG. 3 is a bar diagram graph showing the SO to LD phase transition temperature range of liposomes comprising different phospholipids mixtures assessed from the DSC scans. Grey area indicates the temperature range of 20° C.-39° C.

The thermotropic behavior and thermodynamic parameters of the liposomal combinations were assessed as described in Example 2 and in Materials and Methods. Table 13 summarizes the thermotropic characterization results of the liposomal combinations tested and FIG. 3 shows the SO-LD phase transition temperature range of MLV of different phospholipids mixtures assessed from the DSC scans.

TABLE 13

Thermotropic characterization of MLV of the different mixtures assessed from the DSC scans

| | Thermotropic characterization | | | | | | | | | |
|---|---|---|---|---|---|---|---|---|---|---|
| | Peak 1 (pre-transition) | | | | | Peak 2 (phase-transition) | | | | |
| PC ratio (mol %) | $T_{on}$ (°C.) | $T_{off}$ (°C.) | $T_p$ (°C.) | $T_{1/2}$ (°C.) | ΔH (Cal/mole) | $T_{on}$ (°C.) | $T_{off}$ (°C.) | $T_m$ (°C.) | $T_{1/2}$ (°C.) | ΔH (Cal/mole) |
| DPPC: DMPC mixtures | | | | | | | | | | |
| DPPC (100) | 32.3 | 37.3 | 34.9 | 2.2 | 1983.5 | 40.44 | 42.45 | 41.8 | 1.3 | 7993.7 |
| DMPC/DPPC (10/90) | 28.3 | 33.8 | 30.8 | 2.9 | 1666.2 | 37.77 | 40.91 | 40.0 | 1.9 | 9982.4 |
| DMPC/DPPC (25/75) | 22.6 | 29.8 | 25.8 | 3.2 | 1429.3 | 34.24 | 38.23 | 37.4 | 2.8 | 10363.0 |
| DMPC/DPPC (45/55) | 17.8 | 24.7 | 21.0 | 2.2 | 1030.5 | 30.44 | 35.19 | 33.6 | 3.5 | 9782.1 |
| DMPC (100) | 11.4 | 16.4 | 14.0 | 1.0 | 683.7 | 23.24 | 25.24 | 24.4 | 1.1 | 5394.7 |
| DSPC: DMPC mixture | | | | | | | | | | |
| DMPC/DSPC (75/25) | 11.4 | 17.4 | 14.2 | 4.0 | 369.5 | 24.67 | 34.6 | 27.1 | 2.7 | 10199.9 |
| C15: DMPC mixtures | | | | | | | | | | |
| C15 (100) | 21.7 | 27.3 | 24.6 | 2.2 | 1316.9 | 33.03 | 35.16 | 34.3 | 1.3 | 6716.9 |
| DMPC/C15 (45/55) | 15.9 | 21.0 | 18.1 | 1.7 | 1059.7 | 28.03 | 30.28 | 29.4 | 1.3 | 7767.7 |
| DMPC/C15 (25/75) | 17.9 | 22.9 | 20.4 | 1.2 | 851.1 | 30.35 | 32.12 | 31.3 | 1.2 | 7107.5 |
| D-erythro C16/DMPC mixtures | | | | | | | | | | |
| SPM (100) | 30.2 | 38.8 | 33.9 | 0.8 | 941.5 | 41.14 | 43.24 | 41.8 | 1.0 | 7967.0 |
| D-erythro C16/DMPC (90/10) | 32.5 | 36.0 | 33.8 | 0.7 | 200.2 | 38.36 | 41.91 | 39.7 | 2.2 | 7503.7 |
| D-erythro C16/DMPC (75/25) | 22.3 | 25.8 | 23.8 | 0.5 | 97.5 | 34.7 | 39.77 | 36.5 | 3.1 | 6758.1 |

TABLE 13-continued

Thermotropic characterization of MLV of the different mixtures assessed from the DSC scans

| | Thermotropic characterization | | | | | | | | | |
|---|---|---|---|---|---|---|---|---|---|---|
| | Peak 1 (pre-transition) | | | | | Peak 2 (phase-transition) | | | | |
| PC ratio (mol %) | $T_{on}$ (° C.) | $T_{off}$ (° C.) | $T_p$ (° C.) | $T_{1/2}$ (° C.) | $\Delta H$ (Cal/mole) | $T_{on}$ (° C.) | $T_{off}$ (° C.) | $T_m$ (° C.) | $T_{1/2}$ (° C.) | $\Delta H$ (Cal/mole) |
| D-erythro C16/DMPC (25/75) | 13.9 | 19.1 | 16.6 | 2.9 | 126.9 | 30.91 | 36.19 | 32.1 | 3.2 | 7304.5 |
| D-erythro C16/DMPC (10/90) | 11.4 | 14.8 | 13.0 | 1.3 | 233.9 | 26.68 | 29.72 | 27.5 | 1.7 | 7592.0 |
| DMPC (100) | 11.4 | 16.4 | 14.0 | 1.0 | 683.7 | 23.24 | 25.24 | 24.4 | 1.1 | 5394.7 |

It can be seen that various liposomal combinations, including, for example, DMPC/DPPC (25/75), DMPC/DPPC (45/55), DMPC/DSPC (75/25), DMPC/C15 (45/55), DMPC/C15 (25/75), D-erythro C16/DMPC (75/25), D-erythro C16//DMPC (25/75), and D-erythro C16/DMPC (10/90) have a phase transition temperature of the liposome membranes in the desired 20° C. to 39° C. temperature range.

Example 4

Evaluation of the Liposomal Composition By a Pin-On-Disc Cartilage Abrasion Test Tribological conditions in the knee were simulated in vitro by a pin-on-disc test using porcine cartilage pins sliding against CoCrMo discs. The pin-on-disc tests were carried out on an OrthoPOD machine from Advanced Mechanical Technology Inc. (AMTI), Watertown, Mass. 02472-4800, USA. The machine was heated by a thermostat to ensure a temperature of 37±3° C. inside the liquid. The cylindrical containers were filled with 20 mL of test liquid. The forces applied by each individual holding arm were checked with the pin centered above the disc at 3, 10, 30, 50 and 100 N using a Mecmesin force gauge.

The cartilage pins were retrieved from pig shoulders. The joint capsule was opened using a scalpel to expose the cartilage surface. At least ten cylindrical pins were harvested by using a hollow punch with 5.0 mm inner diameter. Six pins from the same animal, with appropriate length and the least surface inclination, were chosen for each pin-on-disc abrasion test.

Lubrication ability of the pharmaceutical composition of the invention was assessed by measuring subchondral bone mass loss and height loss following 12 hours of wear testing. Six cartilage pins were used for each test whereas three pins were removed after 6 hours and the other three pins were tested for additional 6 hours. Besides determining the weight and mass loss of the pins, the cartilage surfaces were analyzed by an optical profiler before and after the test. The device used was S neox interferometry and confocal microscope (Sensofar, Spain). To determine the roughness parameters, more than 12 line profiles were extracted from the topographies after the form removal. For the illustration of the surface obliqueness, profiles were extracted from the 5× confocal measurements in north-south direction as positioning of the pins was with the highest level facing towards south. For enhanced clarity, these profiles were smoothed and shifted using Kaleidagraph 4.0.

The liposome-based composition comprising mannitol (Formulation #3 from Table 2) was tested in the wear test. This composition was compared to a protein containing liquid, containing 30 g/l of calf serum proteins, EDTA and NaN$_3$, as used for hip simulator test (ISO 14242-1).

Results

Wear Test

Figure 4:
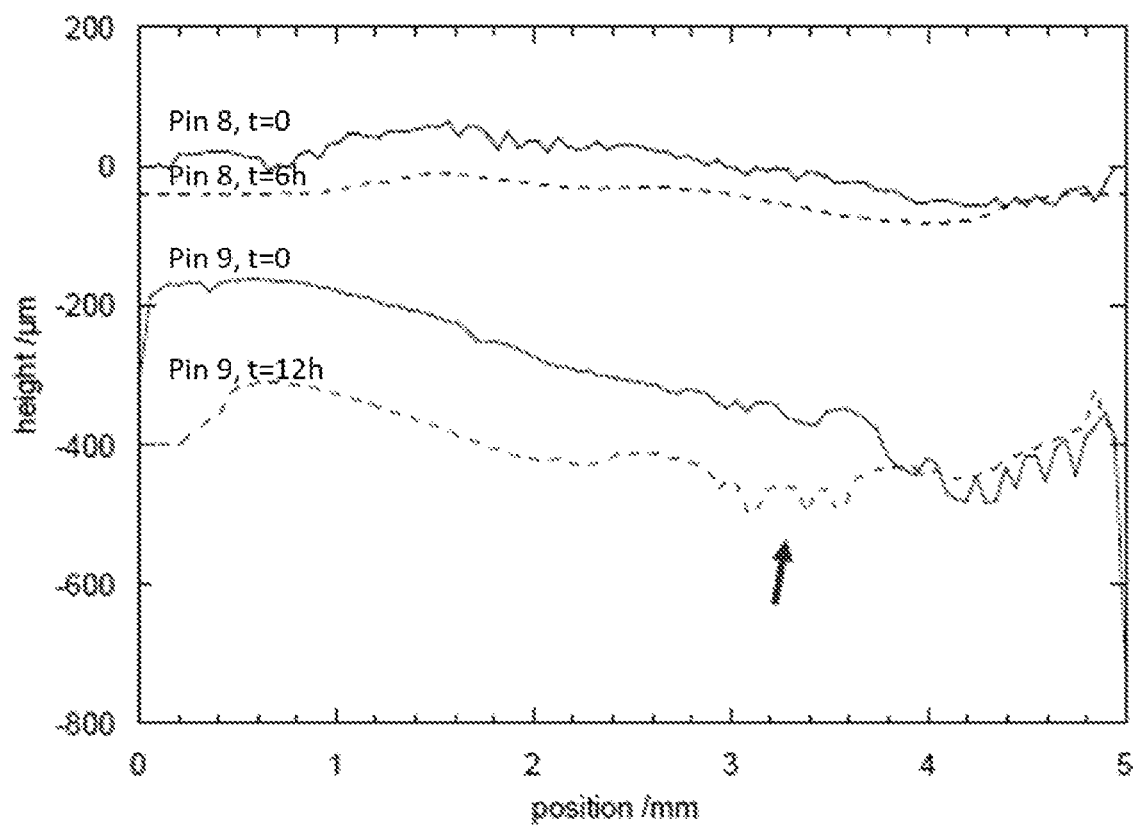
FIG. 4 shows profiles of cartilage pins before and after wear test in protein-based liquid. Position of appearing subchondral bone is marked by arrow. The scale does not show the effective height as the profiles are shifted for better visibility.
Figure 5A:
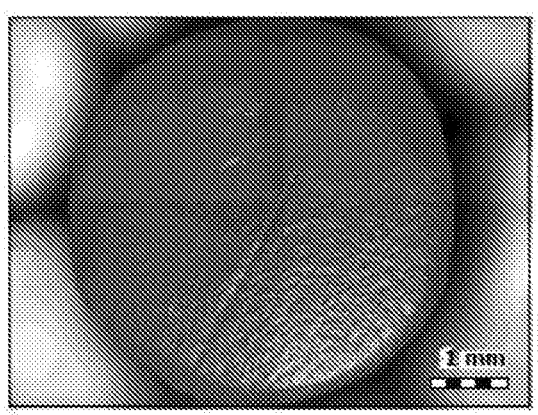
FIG. 5A-5B show optical images of cartilage pin #9 before (FIG. 5A) and 12 hours after (FIG. 5B) wear testing in protein-based liquid. Besides the outer cartilage ring, subchondral bone appeared where cartilage was worn through (indicated by arrow).
Figure 5B:
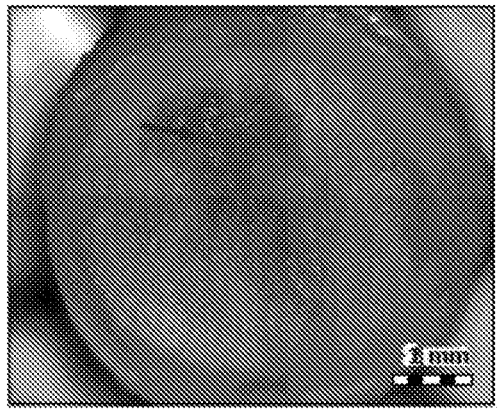

The Pin-on-Disc tests within protein containing liquid revealed wear of the cartilages. Average mass loss of the pins increased from 22 mg after 6 hours to 26 mg after 12 hours of testing. The increase in average height loss of the pins was more pronounced with 0.6 mm after 6 hours and 1.1 mm after 12 hours of wear. The extracted profiles (FIG. 4) show that after 6 hours of wear, the cartilage surfaces had flattened. Some of the cartilage material was moved aside and formed an outer bulge which was only loosely attached to the initial pin. The actual mass loss was therefore underestimated as the weights were determined including the attached bulge. After 12 hours of wear, the three remaining pins showed areas where the cartilage had been worn through and where subchondral bone appeared (FIG. 4 and FIGS. 5A, 5B).

Figure 6:
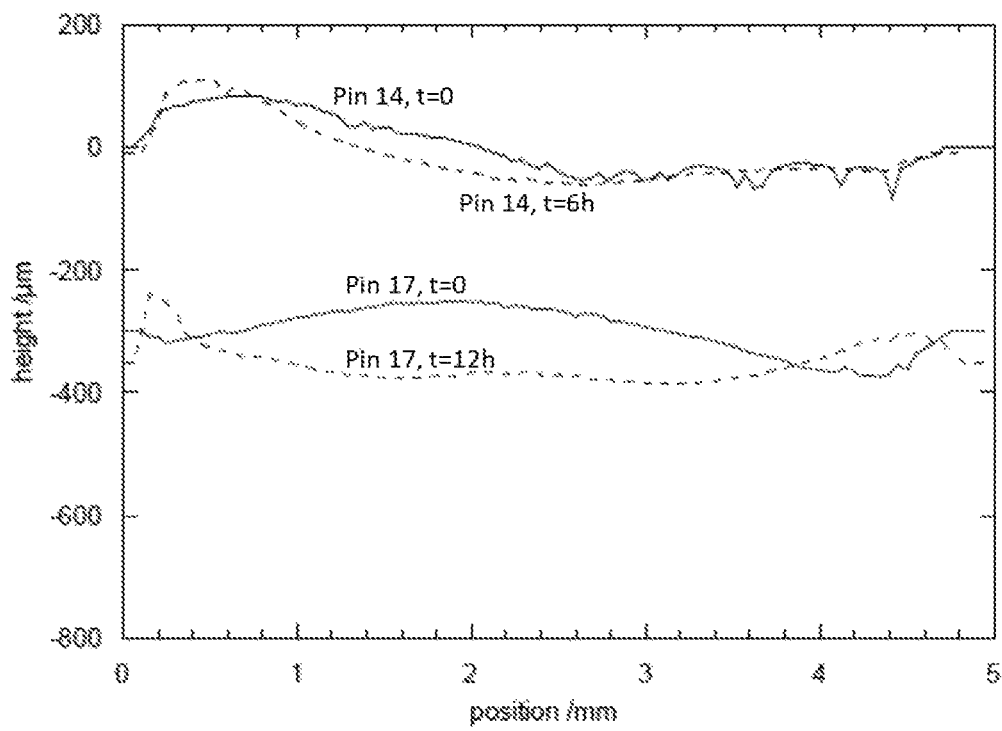
FIG. 6 shows profiles of cartilage pins before and after wear test in liposomal composition. The scale does not show the effective height as the profiles are shifted for better visibility.
Figure 7A:
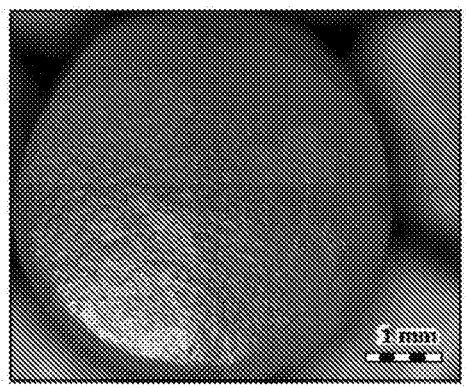
FIG. 7A-7B show optical images of cartilage pin #14 before (FIG. 7A) and 6 hours after (FIG. 7B) wear testing in liposomal composition.
Figure 8A:
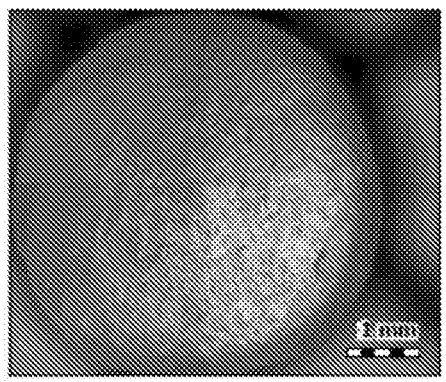
FIG. 8A-8B show optical images of cartilage pin #17 before (FIG. 8A) and 12 hours after (FIG. 8B) wear testing in liposomal composition.
Figure 7B:
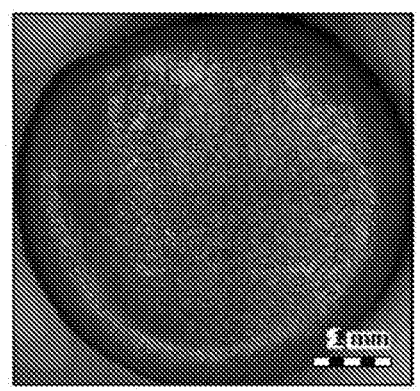
Figure 8B:
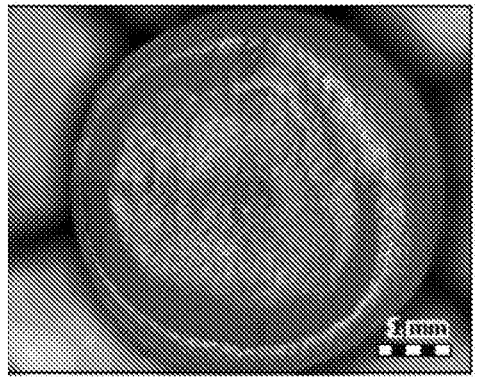

The cartilage pins in the liposomal composition (Formulation #3) showed signs of abrasion after removal. Average mass loss of the pins was 14 mg after 6 hours of wear and remained at that level for the additional 6 hours of wear. The height loss was around 0.3 to 0.4 mm for the two time points. After 6 hours of wear, the cartilage surfaces had flattened (FIG. 6 and FIGS. 7A, 7B) and cartilage material was forming a bulge around the center. After 12 hours of wear, the cartilage surfaces of the remaining pins were still intact and did not show areas with appearing subchondral bone (FIGS. 8A, 8B).

Figure 9A:
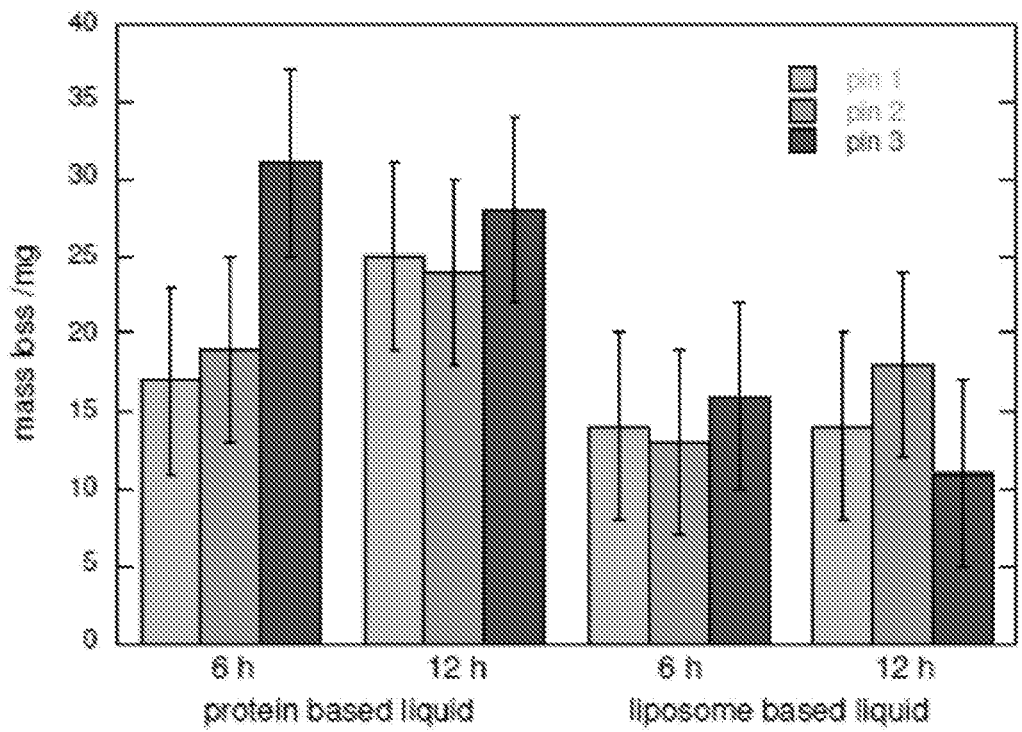
FIG. 9A-9B show a graphical comparison of mass loss (FIG. 9A) and height loss (FIG. 9B) of the protein based vs. the liposomal composition. The error bars are a rough estimate of the measurement precision.
Figure 9B:
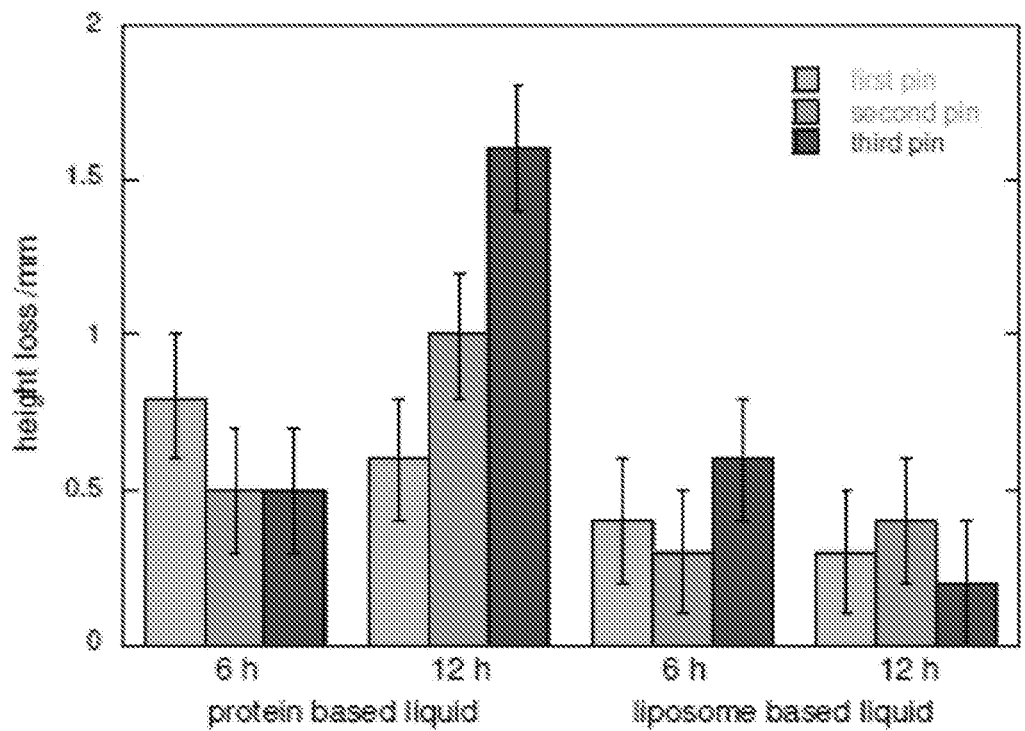

The cartilage pins in protein liquid showed the appearance of subchondral bone after 12 hours of wear testing unlike the pins in liposomal composition where cartilage remained intact throughout the test. Wear seemed to slow down in liposomal composition as no additional mass loss or height loss was observed between 6 and 12 hours The wear results are further illustrated in FIGS. 9A (mass loss) and 9B (height loss). The comparison of the two liquids showed that the liposomal composition led to smaller mass and height loss of the cartilage pins.

Roughness Measurements

Figures 10A, 10B:
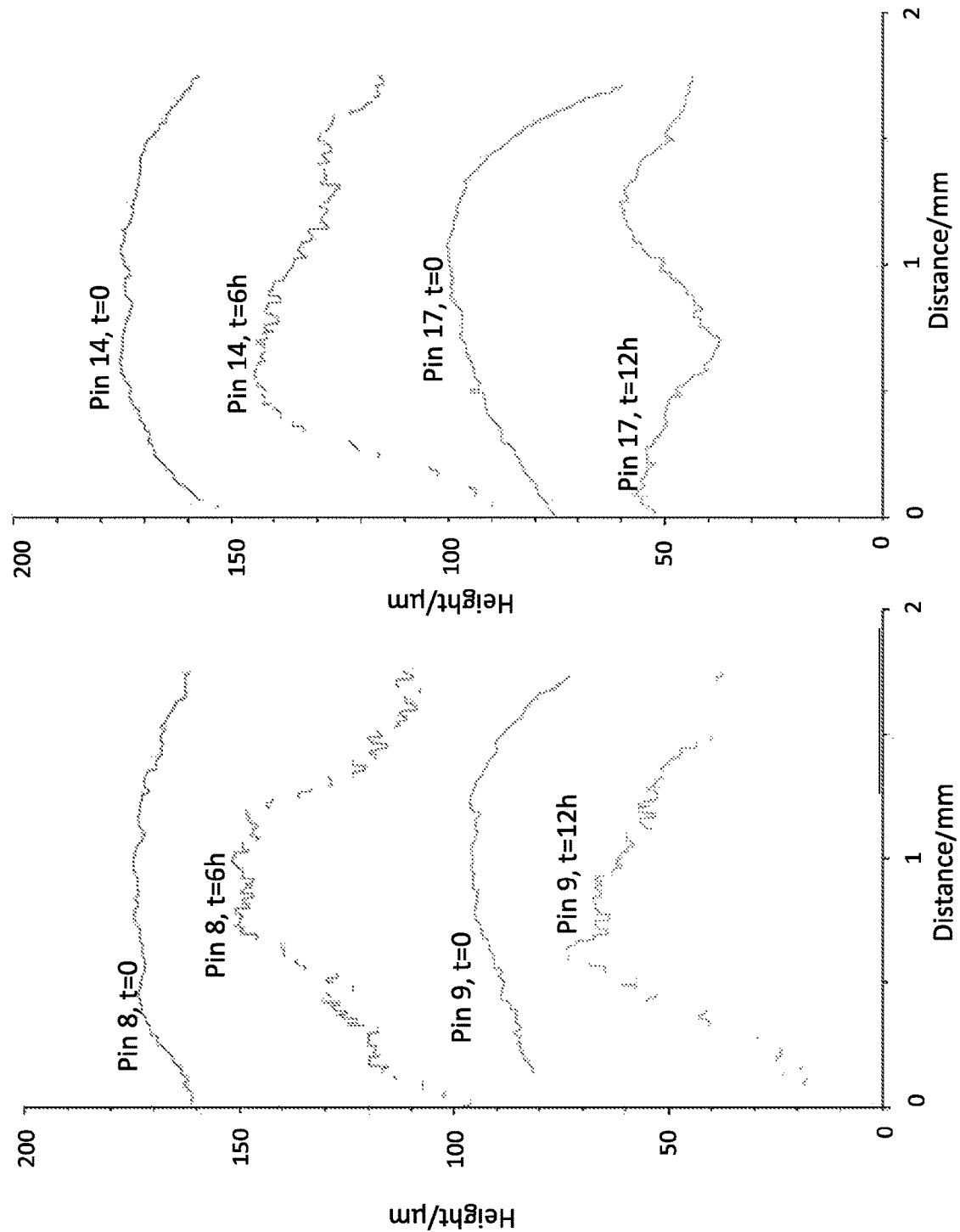
FIG. 10A-10B show profiles of the cartilage surfaces before and after the wear test in protein-based liquid (FIG. 10A) and in liposomal composition (FIG. 10B).

The roughness parameters were determined from a series of extracted profiles based on the interferometry measurements with the DI 10× objective. The measurements were taken in the central part of the pin, well within the contact surface. FIGS. 10A and 10B show exemplary profiles after form removal of the underlying plane.

Figure 11:
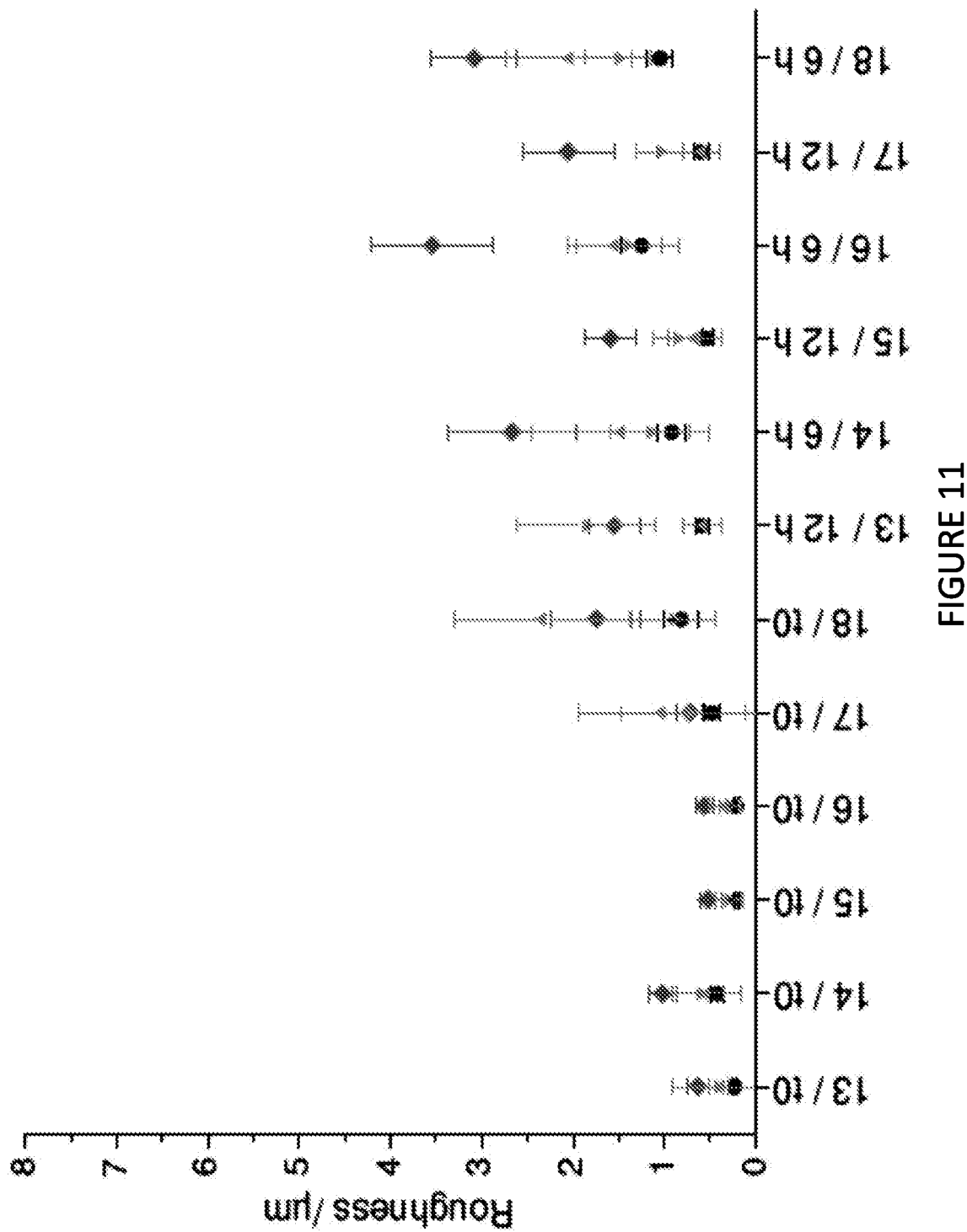
FIG. 11 shows roughness parameters Ra (●), Rk (♦), Rpk (▲) and Rvk (▼), before (t=0) and after wear testing (6 h and 12 h) for pins 13 to 18 tested in the liposomal composition, wherein Ra is an arithmetic mean deviation of roughness profile and Rk is kernel roughness depth (roughness depth excluding the value of the highest peak (Rpk) and the lower valley (Rvk)).

The selected roughness parameters Ra, Rk, Rpk and Rvk are shown in FIG. 11. For the wear tests in the protein-based liquid, a highly significant increase of these parameters due to wear could be observed 2 (p<0.01). For example, the average roughness Ra increased from 0.5±0.2 μm at t=0 to 1.6±0.4 μm for the worn pins and the kernel roughness Rk from 1.4±0.5 μm to 4.5±1.1 μm. For the wear test in the liposomal composition, a smaller but significant increase of the roughness parameters was observed with the exception of Rpk (p>0.2). The average roughness Ra increased from 0.4±0.2 μm to 0.8±0.3 μm and the kernel roughness Rk from 0.9±0.4 μm to 2.4±0.8 μm.

It is appreciated by persons skilled in the art that the present invention is not limited by what has been particularly shown and described hereinabove. Rather the scope of the present invention includes both combinations and sub-combinations of various features described hereinabove as well as variations and modifications. Therefore, the invention is not to be constructed as restricted to the particularly described embodiments, and the scope and concept of the invention will be more readily understood by references to the claims, which follow.

The invention claimed is:

1. A pharmaceutical composition formulated for providing lubrication to a mammalian joint in the form of a dosage unit consisting essentially of:
   liposomes consisting essentially of 1,2-dimyristoyl-sn-glycero-3-phosphocholine (DMPC) and 1,2-dipalmitoyl-sn-glycero-3-phosphocholine (DPPC), wherein said liposomes are multilamellar vesicles (MLV) having at least one membrane and a phase transition temperature in the range of about 20° C. to about 39° C.;
   mannitol in an amount sufficient to reduce local irritation by preventing osmotic shock at a site of administration of the composition; and
   a fluid medium selected from buffer or water in which the liposomes are suspended;
   wherein the pharmaceutical composition is essentially free of hyaluronic acid and any additional pharmaceutically active agents;
   wherein the pharmaceutical composition provides lubrication of a mammalian joint having a temperature which is above the phase transition temperature with the amount of mannitol present to also improve lubrication efficacy of the composition;
   wherein the mannitol is present in a weight percent ranging from about 1% (w/w) to about 7% (w/w), of the total weight of the pharmaceutical composition,
   wherein the weight ratio between the liposomes and mannitol ranges from about 6:1 to about 2:1; and
   wherein the dosage unit of the pharmaceutical composition has from about 30 mg to about 550 mg DPPC, from about 20 mg to about 450 mg DMPC, and from about 20 mg to about 350 mg mannitol.

2. The composition according to claim 1, wherein DMPC is present in the pharmaceutical composition in a weight percent ranging from about 1% (w/w) to about 10% (w/w) and DPPC is present in a weight percent ranging from about 2% (w/w) to about 12% (w/w).

3. The composition according to claim 1, wherein said buffer is a histidine buffer.

4. The composition according to claim 1, having an osmolality in the range from about 200 to about 600 mOsm.

5. The composition according to claim 1, having a pH of about 5-8.

6. The composition according to claim 1, wherein the mole percent ratio of DMPC to DPPC is in the range of about 25:75 to about 70:30.

7. The composition according to claim 6, wherein the mole percent ratio of DMPC to DPPC is about 45:55.

8. The composition according to claim 1, wherein the liposomes have a mean diameter of between about 0.5 μm to about 10 μm.

9. The composition according to claim 1, wherein the at least one membrane has the phase transition temperature of about 30° C. to about 35° C.

10. The composition according to claim 1, wherein the mammalian joint temperature is in the range of about 1-15° C. above said phase transition temperature.

11. The composition according to claim 1, wherein the liposomes are in the form of a suspension.

12. The composition according to claim 1, wherein the composition is in a form suitable for administration selected from the group consisting of intra-articular injection, arthroscopic administration and surgical administration.

13. The composition according to claim 1, wherein the lubrication is for the treatment, management or prevention of an articular disorder or condition or symptoms arising therefrom.

14. A pharmaceutical composition formulated for providing lubrication to a mammalian joint in the form of a dosage unit consisting essentially of:
   liposomes consisting essentially of 1,2-dimyristoyl-sn-glycero-3-phosphocholine (DMPC) and 1,2-dipalmitoyl-sn-glycero-3-phosphocholine (DPPC), wherein said liposomes are multilamellar vesicles (MLV) having at least one membrane and a phase transition temperature in the range of about 20° C. to about 39° C.;
   mannitol in an amount sufficient to obtain an osmolality in the range from about 200 to about 600 mOsm; and
   a fluid medium of a histidine buffer in which the liposomes are suspended;
   wherein the composition has a pH of about 5-8;
   wherein the liposomes have a mean diameter of between about 0.5 μm to about 10 μm;
   wherein the pharmaceutical composition is essentially free of hyaluronic acid and any additional pharmaceutically active agents;
   wherein the pharmaceutical composition provides lubrication of a mammalian joint having a temperature which is above the phase transition temperature with the amount of mannitol present to also improve lubrication efficacy of the composition;
   wherein DMPC is present in the pharmaceutical composition in a weight percent ranging from about 1% (w/w) to about 10% (w/w), DPPC is present in a weight percent ranging from about 2% (w/w) to about 12% (w/w), and mannitol is present in a weight percent ranging from about 1% (w/w) to about 7% (w/w), of the total weight of the pharmaceutical composition;
   wherein the weight ratio between the liposomes and mannitol ranges from about 6:1 to about 2:1; and
   wherein the dosage unit of the pharmaceutical composition has from about 20 mg to about 350 mg mannitol, from about 30 mg to about 550 mg DPPC and from about 20 mg to about 450 mg DMPC.

15. A method for treating pain and/or reducing local irritation in a joint of a mammal, the method comprising: administering into a cavity of the joint the pharmaceutical composition according to claim 1 to provide joint lubrication while preventing osmotic shock at the site of administration due to the presence of mannitol in the composition.

16. The method according to claim 15, wherein the pharmaceutical composition is administered by a route selected from the group consisting of intra-articular injection, arthroscopic administration and surgical administration.

17. The method according to claim 15, wherein the pharmaceutical composition is in a form of a parenteral pharmaceutical composition having a suspension of the liposomes and is administered in a dose of from about 0.5 ml to about 10 ml.

18. A method for treating pain and/or reducing local irritation in a joint of a mammal, the method comprising: administering into a cavity of the joint the pharmaceutical composition according to claim 14 to provide joint lubrication while preventing osmotic shock at the site of administration due to the presence of mannitol in the composition.

19. The method according to claim 18, wherein the pharmaceutical composition is administered by a route selected from the group consisting of intra-articular injection, arthroscopic administration and surgical administration.

20. The method according to claim 18, wherein the pharmaceutical composition is in a form of a parenteral pharmaceutical composition having a suspension of the liposomes and is administered in a dose of from about 0.5 ml to about 10 ml.

* * * * *